US008676606B1

(12) United States Patent
Nadas et al.

(10) Patent No.: US 8,676,606 B1
(45) Date of Patent: Mar. 18, 2014

(54) SYSTEMS AND METHODS FOR PROVIDING COMPREHENSIVE PHARMACEUTICAL CONSULTATIONS

(75) Inventors: Gyula J. Nadas, Wauconda, IL (US); Michael R. Johnson, Hobart, IN (US); Anthony James Fields, Menomonee Falls, WI (US)

(73) Assignee: Walgreen Co., Deerfield, IL (US)

( * ) Notice: Subject to any disclaimer, the term of this patent is extended or adjusted under 35 U.S.C. 154(b) by 258 days.

(21) Appl. No.: 12/917,061

(22) Filed: Nov. 1, 2010

(51) Int. Cl.
*G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | |
|---|---|---|---|
| 6,578,003 B1 | 6/2003 | Camarda et al. | |
| 7,630,788 B1 | 12/2009 | Reese | |
| 2002/0069087 A1* | 6/2002 | Fairley et al. ................... | 705/2 |
| 2002/0069088 A1* | 6/2002 | Berg .................................. | 705/3 |
| 2003/0221687 A1 | 12/2003 | Kaigler | |
| 2003/0236681 A1 | 12/2003 | Ninomiya et al. | |
| 2003/0236683 A1 | 12/2003 | Henderson et al. | |
| 2004/0059634 A1 | 3/2004 | Tami et al. | |
| 2004/0230458 A1* | 11/2004 | Takayama et al. .............. | 705/3 |
| 2004/0260577 A1 | 12/2004 | Dahlin et al. | |
| 2005/0096785 A1 | 5/2005 | Moncrief et al. | |
| 2007/0214009 A1 | 9/2007 | Epstein et al. | |
| 2008/0015897 A1 | 1/2008 | Moradi et al. | |
| 2008/0109252 A1 | 5/2008 | LaFountain et al. | |
| 2008/0228525 A1 | 9/2008 | Weickert et al. | |
| 2009/0048863 A1* | 2/2009 | Kozlowski et al. ............. | 705/2 |
| 2009/0048864 A1* | 2/2009 | Kozlowski et al. ............. | 705/2 |

OTHER PUBLICATIONS

Final Office action for U.S. Appl. No. 11/959,242 dated Dec. 9, 2010.
Final Office action for U.S. Appl. No. 11/959,837 dated Nov. 24, 2010.
Office action for U.S. Appl. No. 11/959,837 dated May 21, 2010.
Office action for U.S. Appl. No. 11/959,242 dated May 26, 2010.
Office action for U.S. Appl. No. 11/959,428 dated Nov. 29, 2010.
Final Office action for U.S. Appl. No. 11/959,305 dated Dec. 27, 2010.
Office action for U.S. Appl. No. 11/959,305 dated May 17, 2010.
Final Office action for U.S. Appl. No. 11/959,425 dated Nov. 26, 2010.
Office action for U.S. Appl. No. 11/959,425 dated Jun. 10, 2010.

* cited by examiner

*Primary Examiner* — Sind Phongsvirajati
(74) *Attorney, Agent, or Firm* — Francis C. Kowalik; Marshall, Gerstein & Borun LLP; Randall G. Rueth

(57) ABSTRACT

Systems and methods of providing comprehensive pharmaceutical consultations are disclosed, including generating a consultation recording block corresponding to a filling of a prescription order for a patient. The consultation recording block may include multiple consultation entries, where each consultation entry corresponds to a particular pharmaceutical consultation that is desired or required to occur in conjunction with the prescription fill. Input corresponding to various fields of various consultation entries may be received and stored. Different fields of different consultation entries corresponding to a particular patient and to a particular prescription order may be displayed, populated, viewed, resolved and authorized by different pharmaceutical personnel at different work flow stages of the filling, and in some cases, one or more consultation entries may be automatically generated and at least partially automatically populated. The techniques described herein allow for more comprehensive pharmaceutical consultations as compared to presently known techniques.

18 Claims, 19 Drawing Sheets

| | | | | | WAIT 2331Min | 6:00AM | | F1 | 212 | F4 | 0 | CMD | 0 | TPR | 0 | PFL | 0 | MSC | 0 |
| | | | | | PAT | 0 Calls | | FILL | 18 | REV | 0 | WCB | 0 | DUR | 1 | OOS | 0 | STATS | |
| Application | Patient | Options | Details | Utilities | Window | PBR | 0 Calls | 1 Pat | 2 Pbr | 3 Plsm | 4 PA | 5 Fax | 6 Store |

Search By
Enter one of the following:

Patient Phone: _____    Patient Last Name: PATIENT

Prescriber Last Name: _____    Rx Status: READY ▼    Rx #: _____    [Search]

— 465    — 468

Work Queue

| Status | E-Pay | Bin | Type | Consult | Promised Time | Patient | Rx Price | Rx # | |
|---|---|---|---|---|---|---|---|---|---|
| READY | | 24 | | | 04/06/09 01:51 PM | PATIENT, ONE | $25.39 | 181092 | METHADO |
| READY | | 24 | | | 04/06/09 01:59 PM | PATIENT, ONE | $72.19 | 181093 | WARFARIN |
| READY | | 24 | | Y | 04/06/09 01:59 PM | PATIENT, PAULA | $50.99 | 181094 | AMOXICIL |
| READY | | 24 | | | 04/06/09 01:59 PM | PATIENT, ONE | $477.89 | 181095 | DIASTAT A |
| READY | | 24 | | | 04/06/09 01:15 PM | PATIENT, ONE | $44.29 | 181096 | PRENATAL |
| READY | | 24 | | | 04/10/09 01:31 PM | PATIENT, TWO | $23.29 | 181164 | LANTUS U |
| READY | | 25 | | | 04/10/09 01:35 PM | PATIENT, TWO | $113.49 | 181165 | ZANTAC 15 |
| READY | | 25 | | | 04/10/09 01:35 PM | PATIENT, TWO | $83.99 | 181166 | ALLEGRA |
| READY | | 26 | | | 04/17/09 02:18 PM | PATIENT, THREE | $6.99 | 181173 | IBUPROFE |
| READY | | 30 | | | 04/08/09 12:59 PM | PATIENT, FOUR | $21.89 | 181138 | BENTYL 10 |
| READY | | 30 | | | 04/08/09 12:59 PM | PATIENT, FOUR | $110.79 | 181139 | XANAX 2M |

— 462

[Comments] [Exceptions...] [Print] [Update Rx...] [Waiter] [Review] [Consult] [Partial Fill] [Close]

— 470

Row 1 of 18                NJW    NJW    OK    3:08 PM

Patient Chart

| Paula Patient | 01/20/1974 | F | (312)555-5555 | 678 Main St | | ANYTOWN | | IL | 60604 |

RPh Consultation Required (1 of 1)

| Px # | Drug | Type | Directions | Qty | DS | Prescriber |
|------|------|------|------------|-----|----|-----------:|
| 123456-12345 | AMOXICILLIN 500MG CAPSULES | NEW | TAKE 1 CAPSULE BY MOUTH THREE TIMES DAILY | 30 | 10 | JANE SMITH |

Initiating Consultation Comments:

01/31/10; 12:47 PM; MRJ; please check with patient to see if she is allergic to amoxicillin. Profile states Cephalexin allergy.

Consultation Resolution:

☐ Consultation Completed  ☐ Patient Declined  ☐ RPh Declined

[ Save and Sign ]  [ Skip Rx ]  [ Close ]

*FIG. 7*

Patient Chart

| Paula Patient | 01/20/1974 | F | (312)555-5555 | 678 Main St | | ANYTOWN | | IL | 60604 |

WAIT 24Min 9:41AM | F1 1 | F4 0 | CMD 0 | TPR 1 | PFL 0 | MSC 0
PAT 0 Calls | FILL 5 | REV 1 | WCB 0 | DUR 0 | OOS 0 | STATS
PBR 0 Calls Activities | Consultation History | Services

RPh Consultation Required (1 of 1):

| Px # | Drug | Type | Directions | Qty | DS | Prescriber |
|---|---|---|---|---|---|---|
| 123456-12345 | AMOXICILLIN 500MG CAPSULES | NEW | TAKE 1 CAPSULE BY MOUTH THREE TIMES DAILY | 30 | 10 | JANE SMITH |

Initiating Consultation Comments:

01/31/10; 12:47 PM; MRJ; please check with patient to see if she is allergic to amoxicilin. Profile states Cephalexin allergy.

Consultation Resolution:

☑ Consultation Completed  ☐ Patient Declined  ☐ RPh Declined

Checked with patient, has has before many times without reaction. Warned patient of cross-over reactivity and what to do if it happens.

[Save and Sign]  [Skip Rx]  [Close]

Patient Chart

Paula Patient | 01/20/1974 | F | (312)555-5555 | 678 Main St | ANYTOWN | IL | 60604

WAIT 20Min 9:26 AM
PAT 0 Calls
PBR 0 Calls

F1 1 | CMD 0 | TPR 1 | PFL 0 | MSC 0
F4 1 | WCB 0 | DUR 0 | OOS 0 | STATS
FILL 4 | REV 0

Activities | Consultation History | Services

RPh Consultation Required (1 of 1)

| Px # | Drug | Type | Directions | Qty | DS | Prescriber |
|---|---|---|---|---|---|---|
| 123456-12345 | AMOXICILLIN 500MG CAPSULES | NEW | TAKE 1 CAPSULE BY MOUTH THREE TIMES DAILY | 30 | 10 | JANE SMITH |

Initiating Consultation Comments:

01/31/10; 12:47 PM; MRJ; please check with patient to see if she is allergic to amoxicillin. Profile states Cephalexin allergy.

Consultation Resolution:
☑ Consultation Completed  ☐ Patient Declined  ☐ RPh Declined Consultation Completed Save and Sign | Skip Rx | Close 480a
482
485
488
490a
490b
500

FIG. 11

DUR Stage — 530

| | | | WAIT 20Min | 9:26 AM | | F1 | 1 | F4 | 0 | CMD | 0 | TPR | 1 | PFL | 1 | MSC | 0 |
| | | | PAT | 0 Calls | | FILL | 5 | REV | 1 | WCB | 0 | DUR | 0 | OOS | 0 | STATS | |
| Paula Patient | 01/20/1974 | F | (312)555-5555 | 678 Main St | | | | ANYTOWN | | | | | | IL | 60604 | | |

Activities | Consultation History | Services

RPh Consultation Required (1 of 2) — 532

| Px # | Drug | Type | Directions | Qty | DS | Prescriber |
|---|---|---|---|---|---|---|
| 123456-12345 | AMOXICILLIN 500MG CAPSULES | NEW | TAKE 1 CAPSULE BY MOUTH THREE TIMES DAILY | 30 | 10 | JANE SMITH |

— 535

Initiating Consultation Comments:

02/01/10; 11:47 AM; MRJ; Patient is on warfarin 2mg. Called MD, states ok to take. Let patient know S&S of an increased anticoagulant effect.

— 538

Consultation Resolution: — 545a
☐ Consultation Completed  ☐ Patient Declined  ☐ RPh Declined — 545b

DUR Interaction Details — 540

| Type | Severity | Rx Number | Rx Date | Overriden |
|---|---|---|---|---|
| DRUG / DRUG-WARFARIN SOD 2MG TABLETS(PURPLE) | MAJOR | 761195 | 01/25/2010 | Y |

[Save and Sign]  [Skip Rx]  [Close]

FIG. 12

Patient Chart — 560

Paula Patient | 01/20/1974 | F | (312)555-5555 | 678 Main St | ANYTOWN | IL | 60604
WAIT 24Min 9:41AM | PAT 0 Calls | PBR 0 Calls
F1 1 | F4 0 | CMD 0 | TPR 1 | PFL 0 | MSC 0
FILL 5 | REV 1 | WCB 0 | DUR 0 | OOS 0 | STATS Activities | Consultation History | Services — 562

RPh Consultation Required (2 of 2)

| Px # | Drug | Type | Directions | Qty | DS | Prescriber |
|---|---|---|---|---|---|---|
| 123456-12345 | DIASTAT ACUDIAL 10MG GEL KIT | NEW | USE AS DIRECTED | 1 | 10 | JANE SMITH |

— 565

Initiating Consultation Comments:

Diastat Consultation. Complete the activity below and then record the resolution to save.

— 568

Consultation Resolution: ☑ Consultation Completed  ☐ Patient Declined  ☐ RPh Declined — 572

Consultation Completed

— 570

(Note: all questions should be answered "yes"); RPH: Did you open the bag, remove the product and take out the card from the plastic package?    ⊙ Yes  ○ No RPH: Did you review the instructions and lock BOTH syringes at the appropriate dose (green band should be visible on BOTH syringes)?    ⊙ Yes  ○ No RPH: Did you confirm with the patient that both doses were locked for the appropriate dose (show patient the green band on the syringe)?    ⊙ Yes  ○ No Save and Sign — 575    Skip Rx    Close

Audit / Board of Pharmacy Inspection Report

Rx#: 12345-6     Store#: 12345     Sold Date: 10/21/2009

Annotations
1. "warned md of d-d interaction. Told me to dispense it and he would monitor patient - by MRJ on 10/21/2009 09:06:17 at 55555

Prescription Information — 642

632
Patient
Name: Paula Patient
Address:
678 Main St.,
Anytown, IL. 60604
Date of Birth: 01/20/1974
Allergies/Health Conditions: No known allergies 635
Drug
Drug: ALLOPURINOL 100MG TABLETS
MFG: MY MANUFACTURER
NDC: 00378-0137-01
Generic for:
Drug Class: RX
Directions: TK I TPO QD
Qty: 100   Days Supply: 100
Original Date: 10/21/2009 09:12
Refills remaining when entered: 0

638
Prescriber
Name: DR intercom
DEA#:
Address:
453 Washington st.
Anytown, IL. 60604
(123)456-7890

640
Fill History
Scanned by M.R. JOHNSON on 10/21/2009 09:04:49 at 59393
Entered by M.R. JOHNSON on 10/21/2009 09:12:53 at 59393
Pat/Pbr rev by M.R. JOHNSON on 10/21/2009 09:12:58 at 59393
Data rev by M.R. JOHNSON on 10/21/2009 09:12:58 at 59393
Scale process overridden.
Prod rev by M.R. JOHNSON on 10/21/2009 09:13:45 at 59393
Sold Date 10/21/2009 09:15:37
RPH of Record: M.R. JOHNSON

Consultation Information

645

DUR
DUR Type: 03
DUR Severity: 3
DUR Overridden: Y
DUR Overridden completed by M.R.JOHNSON on 10/21/2009 09:13:36 at 59393
DUR Intervention Comment Code: 2
DUR Comment: 10/21/2009; 9:13 AM; MRJ; PATIENT CONSULTED WILL WARN PATIENT

*FIG. 15A*

| | |
|---|---|
| Consultation Information | |
| Consultation Required: Y<br>Consultation Type: PRODUCT REVIEW<br>Initiating<br>　RPh: M.R. Johnson on 12/01/09 1:45 PM at store#12345<br>　Comments: 12/01/09; 1:45 PM; MRJ; Drug; Please check with patient to see if she has taken amoxicillin before.<br>Resolution<br>　RPh: P.T. PILL on 12/02/09 9:54 AM at store#12345<br>　Comments: 12/02/09; 9:54 AM; PTP; Patient Declined | 648 |
| Consultation Required: Y<br>Consultation Type: SYSTEM GENERATED<br>Initiating<br>　Comments: 12/01/09; 1:45 PM; Diastat Consultation<br>Resolution<br>　RPh: P.T. PILL on 12/02/09 9:55 AM at store#12345<br>　Comments: 12/02/09; 9:55 AM; PTP; Discussed with patient | 650 |

CONSULTATION COMPLIANCE SEARCH — 670

Enter desired search parameters:

Location: 88888 — 675a
Type: MANUAL — 675b
Status: Patient-Declined — 675c
Date: From: 01/01/07  To: 03/31/07 — 675d

GO — 672

RESULTS:

| DATE (678a) | PATIENT (678b) | DRUG (678c) | WORK FLOW STAGE (678d) | RPh (678e) |
|---|---|---|---|---|
| 4/06/09 | P. Patient | METHADONE | DUR | MAH |
| 4/06/09 | C. Chan | WARFARIN | Data review | TKD |
| 4/06/09 | P. Patient | AMOXICILLIN | DUR | MLT |
| 4/06/09 | L. Lee | DIAZEPAM | Rx Fill | MAH |
| 4/06/09 | S. Smith | PRENATAL | 3rd Party | MAH |
| 4/10/09 | P. Patient | ATORVASTATIN | DUR | TKD |
| 4/10/09 | C. Chan | RANITIDINE | Clinical | MLT |
| 4/10/09 | L. Lee | FEXOFENADINE | Clinical | MLT |
| 4/10/09 | M. Makov | IBUPROFEN | Rx Fill | TKD |
| 4/13/09 | S. Sokol | BENAZEPRIL | Data Entry | MLT |
| 4/13/09 | Z. Zak | ALPRAZOLAM | DUR | MLT |

*FIG. 15C*

SYSTEMS AND METHODS FOR PROVIDING COMPREHENSIVE PHARMACEUTICAL CONSULTATIONS

FIELD AND BACKGROUND OF THE DISCLOSURE

1. Technical Field

The instant disclosure generally relates to pharmaceutical consultations, and in particular, to providing comprehensive pharmaceutical consultations.

2. Background

Currently known techniques for providing pharmaceutical consultations are typically end-loaded. For example, when a prescription order is filled at a pharmacy or other entity licensed to dispense prescription drugs and medications, a consultation is typically conducted when the prescription order is picked up and paid for. At this time, a pharmacist consults with the patient or with the patient's representative (e.g., a party picking up the prescription for the patient) regarding the use and storage of the drug or medication, allergies, interactions with foods, other drugs, or over-the-counter products, and the like. During such an end-loaded consultation, the pharmacist or authorizing party must remember to cover all aspects of consultation (e.g., allergies, currently prescribed medications, interactions, use, storage of prescription, etc.), and in particular, must remember to cover aspects that are required for medical, legal, and/or insurance compliance reasons. The resolution of all aspects of the pharmaceutical consultation is recorded in conjunction with the sale and delivery of the filled prescription order.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Embodiments of a method for providing comprehensive pharmaceutical consultations are disclosed. The method may include generating a consultation recording block corresponding to a filling of a prescription order for a drug prescribed for a patient. The consultation recording block may include two or more consultation entries each corresponding to a consultation that is desired to or is required to occur in conjunction with the filling of the prescription order. Each consultation entry may include a plurality of fields or portions for receiving and storing consultation information, such as fields corresponding to a consultation status, a consultation resolution, consultation comments, and/or a consultation authorization. The method may include storing the consultation recording block, displaying one or more of the consultation entries, receiving information corresponding to at least one portion or field of the displayed consultation entry or entries, and storing the received information. The consultation block or one of its associated consultation entries may be generated based on a user request, or may be automatically generated. In some embodiments, different consultation entries may be created, accessed, viewed, modified, or authorized by different pharmaceutical personnel at different stages of a work flow corresponding to the filling of the prescription order.

Embodiments of a system for providing comprehensive pharmaceutical consultations may include a computing device including a memory and a processor, a display device, and computer-executable instructions stored on the memory of the computing device and executable by the processor to generate a consultation recording block corresponding to a filling of a prescription order for a drug prescribed for a patient. The consultation recording block may include two or more consultation entries, where each consultation entry may correspond to a different consultation associated with the prescription order. Each consultation entry may include at least a status field and an authorization field. The computer-executable instructions may further be executable to store the consultation recording block, display at least a portion of the two or more consultation entries on a user interface screen, receive information corresponding to the displayed at least a portion of the two or more consultation entries, and populate corresponding fields of the two or more consultation entries of the consultation recording block with the received information. In some embodiments, the system may include a user input interface device and at least one or more databases. In some embodiments, the system may be included in a pharmaceutical enterprise computing system.

Embodiments of another system for providing comprehensive pharmaceutical consultations may include a computing device and a consultation recording block corresponding to a filling of a prescription order for a drug prescribed for a patient. The consultation recording block may include two or more consultation entries, where each of the consultation entries corresponds to a different consultation occurring during the filling of the prescription order. Each of the consultation entries may include at least a status portion for indicating a status of a consultation, a resolution portion for indicating a resolution of a respective consultation, a comment portion for displaying stored information corresponding to the drug, and an authorization portion for receiving an authorization of the respective consultation. The system may include a display device for viewing the consultation block or one of its entries, a user input interface for entering information corresponding to the consultation block or one of its entries, and a data storage entity that stores the consultation recording block and any information received with respect to the consultation recording block.

BRIEF DESCRIPTION OF SEVERAL VIEWS OF THE DRAWINGS

Each of FIGS. 4 through 14 and FIGS. 15A-15C depicts a different example screen shot that may be displayed on the system of FIG. 1;

DETAILED DESCRIPTION OF THE PREFERRED EMBODIMENTS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Any or all of the contents of the present disclosure may operate in conjunction with any or all of the contents of the disclosure of co-pending U.S. patent application Ser. No. 12/917,156 entitled "SYSTEMS AND METHODS OF IMPROVING THE EFFICIENCY OF PHARMACEUTICAL CONSULTATIONS," filed concurrently herewith and the contents of which are hereby incorporated by reference in their entirety. Additionally or alternatively, any or all of the contents of the present disclosure may operate in conjunction with any or all of the contents of the disclosure of co-pending U.S. patent application Ser. No. 12/917,147 entitled SYSTEMS AND METHODS FOR DETERMINING PHARMACEUTICAL CONSULTATION COMPLIANCE," filed concurrently herewith and the contents of which are hereby incorporated by reference in their entirety.

Figure 1:
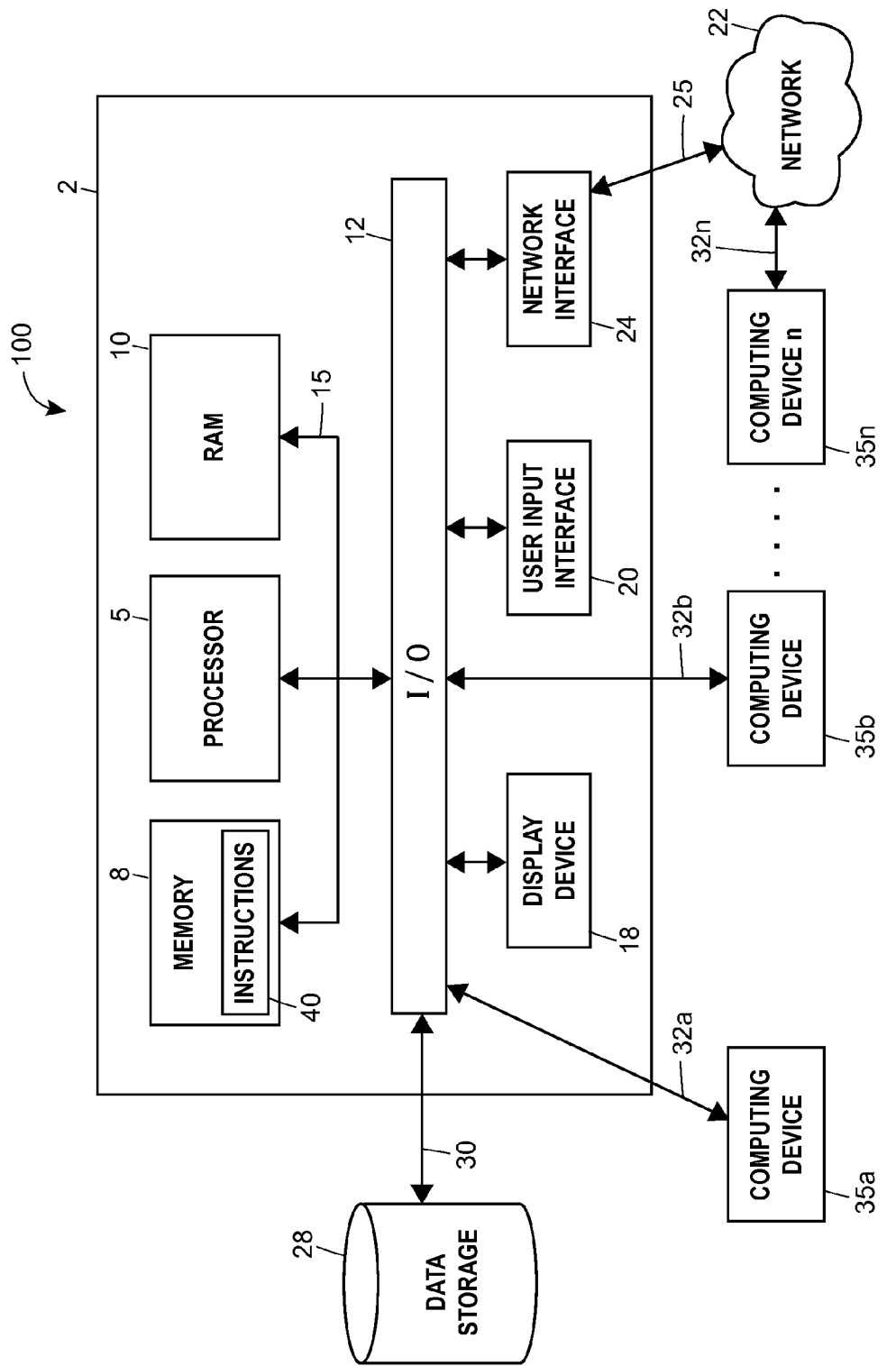
FIG. 1 is a block diagram of an example system for providing comprehensive pharmaceutical consultations.

FIG. 1 is a block diagram of an example system 100 for providing comprehensive pharmaceutical consultations. As used herein, the terms "pharmaceutical consultation" or "consultation" are interchangeably used and refer to a consultation, conference or discussion between an employee or representative of a pharmaceutical enterprise and a customer (who may be a patient or a patient's representative). A pharmaceutical consultation may typically (but not necessarily) occur in conjunction with a filling of a prescription order for the patient. A pharmaceutical consultation may be performed in person, via the telephone, via computers or computing devices, or by using any other known communication medium. Additionally, as used herein, the term "pharmaceutical enterprise" refers to an enterprise that is licensed to dispense prescribed pharmaceutical products such as drugs, medicaments, durable medical equipment, and the like. A pharmaceutical enterprise may be commercial or not-for-profit, and may provide or vend other products in addition to the prescribed pharmaceutical products. A pharmaceutical enterprise may include one or more physical locations, including local store fronts, space within another commercial or not-for-profit enterprise (e.g., within a discount store, hospital, school, nursing home, etc.), a mail-order center, a call-in center, a warehouse, a mobile location, or an Internet or computer-order center. Further, as used herein, the term "pharmaceutical enterprise computing system" may be a computing system that is owned and/or operated by a pharmaceutical enterprise to aid pharmaceutical enterprise employees and representatives to fill and dispense prescribed pharmaceutical products and other products. A pharmaceutical enterprise computing system may include at least one computing device, database, display device, and user input interface device. Typically, each location of a pharmaceutical enterprise may have a local instance of (or local access to) a pharmaceutical enterprise computing system. In some embodiments, local instances of a pharmaceutical enterprise computing system may be networked.

In FIG. 1, the system 100 for providing comprehensive pharmaceutical consultations may include a first computing device or computer 2. Generally, the system 100 may be used during stages of a work flow corresponding to filling prescriptions, but the system 100 may also be used during other processes and operations of a pharmaceutical enterprise. The system 100 may be located in and operated by a pharmaceutical enterprise location. For clarity's sake, the disclosure refers to the pharmaceutical enterprise location or environment in which the system 100 operates as a "pharmacy," but it is understood that the term "pharmacy" as used herein may include any pharmaceutical enterprise location or group of locations. In some embodiments, the system 100 for providing comprehensive pharmaceutical consultations may be included in at least a portion of a pharmaceutical enterprise computing system or at an instance of a pharmaceutical enterprise computing system that is located at a pharmaceutical enterprise location.

The system 100 may provide advantages over currently known pharmaceutical consultation techniques. Currently known techniques for pharmaceutical consultations typically require a pharmaceutical enterprise employee or representative (who is usually not licensed as a pharmacist) to receive and initiate a filling of a prescription order. When the prescription order is ready to be picked up or delivered, a consultation with a licensed pharmacist typically must occur. For example, just prior to receiving payment for the prescription order and giving the filled order to a customer (such as during a product review stage), the customer and the non-licensed pharmaceutical enterprise employee must wait until a licensed pharmacist is available to provide the consultation. The pharmacist must record a resolution to the consultation before the non-licensed employee can continue with receiving payment for the prescription order. The sequential, first-in-first-out nature of current pharmaceutical consultation processes is inefficient and depends largely on bandwidths of registered pharmacists to perform administrative tasks.

The system 100, however, may allow for more efficiencies while performing pharmaceutical consultations. Instead of performing pharmaceutical consultations during a product review stage or just prior to receiving payment, the system 100 may allow for a pharmaceutical consultation to occur during any stage of a work flow corresponding to a filling of a prescription order. In fact, the system 100 may allow for multiple consultations to occur during the filling of a single prescription order, and in some cases, the multiple consultations may even be performed by different parties through the filling process for a single prescription order. All consultations may be recorded and tracked so that at any time during the fill process, any user (e.g., pharmaceutical enterprise employee or pharmaceutical enterprise representative) may easily determine the progress of the fill, the status of associated consultation requirements and their resolutions. These capabilities of the system 100 and other capabilities may allow a pharmaceutical enterprise to make more effective use of its personnel, may help to enforce best practices and compliance with legal, insurance and company requirements, and may also allow the pharmaceutical enterprise to provide a more satisfying customer experience. Examples of these advantages are discussed in later sections of the detailed description.

Turning back to the embodiment of system 100 shown in FIG. 1, for the sake of illustration, a simplified block diagram of the computing device or computer 2 is used to illustrate the principles of the instant disclosure. However, such principles may apply equally to other electronic devices, including, but not limited to, cellular telephones or other wireless devices, personal digital assistants, media players, appliances, gaming systems, entertainment systems, set top boxes, and automotive dashboard electronics, to name a few. The computer 2 may include a processor 5 (may be called a microcontroller or a microprocessor) for executing computer executable instructions, a program memory 8 for permanently storing data related to the computer executable instructions, a random-access memory (RAM) 10 for temporarily storing data related to the computer executable instructions, and an input/output (I/O) circuit 12, all of which may be interconnected via an address/data bus 15.

It should be appreciated that although only one processor 5 is shown, the computer 2 may include multiple processors 5. Similarly, the memory of the computer 2 may include multiple RAMs (Random Access Memories) 10 and multiple program memories 8. The RAM(s) 10 and program memories 8 may be implemented as semiconductor memories, magnetically readable memories, optically readable memories, and/or other tangible, non-transitory computer-readable storage media, for example. Additionally, although the I/O circuit 12 is shown as a single block, it should be appreciated that the I/O circuit 12 may include a number of different types of I/O circuits. For example, a first I/O circuit may correspond to a display device 18, and the first or a second I/O circuit may correspond to a user input interface 20. The user input interface 20 may be, for example, a keyboard, a mouse, a touch screen, a voice activation device, or any other known user input interface device. In some embodiments, the display device 18 and the user input interface 20 may be jointly incorporated in a single physical device. The computing device 2 may also include other elements common to general purpose computing devices.

The computing device or computer 2 may be operatively connected to a network 22 via a network interface 24 and a link 25. The network 22 may be a private network, a public network, or some combination of the two. The network 22 may be a client-server network, a peer-to-peer network, an Ethernet network, a cloud computing network, or any other known type of network in which computing devices are enabled to communicate. In some embodiments, the network 22 may include more than one network. The link 25 may be as simple as a memory access function or an Ethernet connection, and/or the link 25 may be a wired, wireless, or multi-stage connection. Many types of links are known in the art of networking and may be used in conjunction with the computing device 2. In some embodiments, at least one of display device 18 or the user input interface 20 may be remotely connected to the computing device 2 using the network 22 and the link 24.

The processor 5 may be operatively connected to a database or storage entity 28 via a link 30. Similar to the link 25, the link 30 may be any type of link known in the art. In some embodiments, the link 30 may be the same link as the link 25, and the processor 5 may access the data store 28 via the network 22. In some embodiments, the data storage entity 28 may be contained within the computing device 2. In some embodiments, the data storage entity 28 may be a plurality of databases or data storage entities.

The computing device 2 may be in communicative connection with a plurality of other computing devices 35a-35n via links 32a-32n. Each of the computing devices 35a-35n may be associated with pharmaceutical consultations. For example, a computing device 35a may correspond to another location of the pharmaceutical enterprise computing system. A computing device 35b may correspond to a server for performing drug utilization review. Another computing device 35n may provide access to data banks of patient or drug information. Similar to the links 25 and 30, each of the links 32a-32n may be any type of link known in the art, such as a direct link, wired, wireless or other type of link. In some embodiments, the computer 2 may communicate with one or more of the computing devices (e.g., computing device 25n) via the network 18. Although not illustrated, the other computing devices 35a-35n may each also include elements typically found in general computing devices and similar to the computer 2, such as a memory, a processor, a RAM, a bus, a display, a user input interface, a network interface, and other elements.

The computing device 2 may include one or more sets of computer executable instructions 40 providing comprehensive pharmaceutical consultations. As used herein, the terms "computer-executable instructions," "computer executable instructions," and "instructions" are used interchangeably. The instructions 40 may be stored on the memory 8 and executable by the processor 5 to generate one or more consultation recording blocks or consultation blocks for use in providing comprehensive pharmaceutical consultations.

Figure 2:
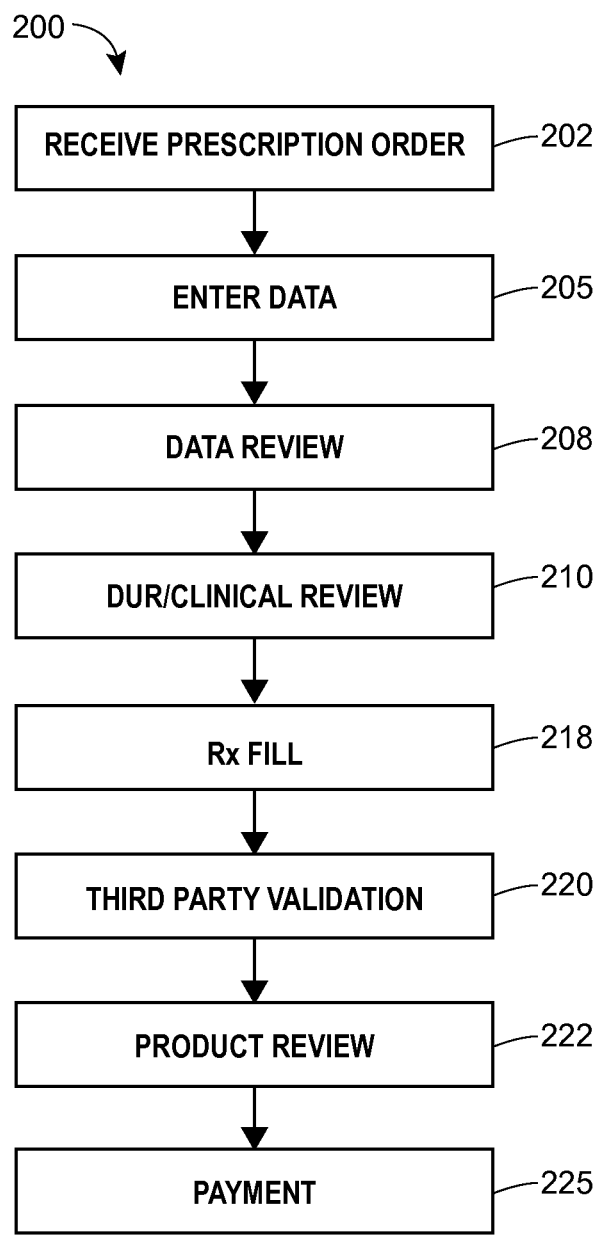
FIG. 2 illustrates an embodiment of stages of a work flow corresponding to a filling of a prescription order.

A pharmaceutical consultation may occur during any stage of a work flow corresponding to a filling of a prescription order. FIG. 2 illustrates one possible embodiment of such a work flow 200 that includes a plurality of work flow stages 202-225. The work flow 200 may operate in conjunction with the system 100 of FIG. 1, or the work flow 200 may operate in conjunction with alternative or additional suitable systems for filling prescription orders or and/or for providing comprehensive pharmaceutical consultations. In one possible embodiment, the computing device 2 of the system 100 may be used to track progress through at least some of the stages 202-225 of the work flow 200. In some embodiments, the computing device 2 executes at least a portion of one or more of the stages 202-225.

A stage 202 of the work flow 200 may include receiving a prescription order 202. The prescription order may be received manually or electronically at a store front pharmacy. For example, a prescription order may be transmitted electronically over a network from a physician's office to the store front pharmacy. In another example, a written prescription order may be mailed to a mail-order pharmacy location. In some examples, a manual prescription order may be converted to an electronic format (such via an image scan, OCR (Optical Character Resolution) conversion, or manual data entry), and the electronically formatted prescription order may be received. During the stage 202, a pharmaceutical consultation may be flagged as being desired, for example, if the prescription order is illegible, if a prescribing physician is shown as having a revoked license, or some other condition.

A stage 205 of the work flow 200 may include entering data corresponding to the prescription order, such as into a pharmaceutical enterprise computing system, or into the system 100. The data may be entered via key board or mouse user action (such as by a pharmaceutical enterprise employee if a manual prescription order is presented), or the data may be downloaded or otherwise entered electronically from an electronic prescription order. The data may be entered into a database corresponding to prescription orders and/or a database corresponding to patients serviced by the pharmacy. In some embodiments, the database corresponding to the prescription orders and/or the database corresponding to patients serviced by the pharmacy may be the database 28 or some other database that is accessible to the computing device 2.

A stage 208 of the work flow 200 may include a data review stage. A data review stage 208 may include validation or verification that the data entered in the stage 205 matches the actual received prescription. Typically, a licensed pharmacist may be mandated to perform at least a portion, if not all, of the data review stage 208.

A stage 210 of the work flow 200 may include a Drug Utilization Review (DUR) stage, also referred to as a clinical review stage. A DUR, as commonly known, is a review of drugs used in a population (e.g., a state, a country, an age group, subscribers of a health insurance plan, etc.) to determine its effectiveness, its potential dangers, any problems with drug interaction, and other issues. Usually, a review board may generate a DUR database for use by pharmacies and other health professionals. Dispensing entities may be legally required to provide a DUR review against one or more DUR databases so that any potential issues may be discovered and resolved during the filling of a prescription order. Review boards may operate at a country, state or other governmental level. Accordingly, the DUR or clinical review stage 210 of the work flow 200 may include accessing a DUR database to review the drug prescribed in the prescription order and a profile of the patient for which the drug was prescribed (e.g., age, gender, chronic conditions, other medications, etc.) based on legally determined rules or guidelines. For example, if a particular patient is a hemophiliac, and a particular drug is shown in a DUR database as potentially increasing blood flow, the DUR stage 210 may highlight or flag this potential conflict. The DUR database may be included in the database 28, or the DUR database may be a different remote or local database that is accessible by the computing device 2 or any other connected computing device.

In addition to mandated or board required DUR review, the DUR or clinical review stage 210 may additionally analyze prescription and patient data to determine any further possible points to flag or to cover during a pharmaceutical consultation based on rules or guidelines recommended by the pharmaceutical enterprise. As an example of such a clinical rule or guideline, a parent company of a local store front pharmacy may require all storefronts to follow flagging requirements that are more stringent than required by a DUR, such as requiring dispensing agents to ask all female patients if they are pregnant when filling certain prescription drugs. In another example, a parent company of a local store front may add additional guidelines or detail for user convenience or comfort, such as requiring pharmaceutical personnel to recommend taking a particular drug at least two hours after eating rather than just "between meals." The clinical rules or guidelines may be stored in the DUR database or in a clinical review database separate from the DUR database.

A stage 218 of the work flow 200 may include a physical filling of the prescription order. During the prescription order fill stage 218, for example, the prescribed drug may be measured, counted, or otherwise prepared, and the prescribed drug may be packaged for dispensing. An accompanying label and instruction sheet may be included.

During a stage 220 of the work flow 200, third party provider information (e.g., Medicare, insurance companies, etc.) may be validated. During the third party validation stage 220, not only may third party provider information be validated for correctness and eligibility, but other information from the third party that may impact the filling of the prescription order may be obtained. For example, the third party validation stage 220 may determine that a third party provider only will cover generic drugs, or that a deductible has been reached.

A stage 222 may include a product review stage. During the product review stage 222, a validation or a verification of packaged prescription contents may be performed to ensure that the contents match the prescription order that was originally received at the stage 202, and that the contents also match the label from the prescription fill stage 218. Typically, a licensed pharmacist may be mandated to perform at least a portion, if not all, of the product review stage 222. Additionally, for currently known data flows, the pharmacist typically performs a pharmaceutical consultation with the patient or with the patient's representative in conjunction with the product review stage 222 or just prior to the next stage 225. The next stage 225 may include a payment stage during which payment for the filled prescription order may be collected or payment arrangements may be finalized with the patient or the patient's representative.

Although the embodiment illustrated in FIG. 2 depicts a particular ordering of the stages 202-225, in other embodiments, a different ordering may be possible. In some embodiments, one or more stages may be omitted or combined. Generally, however, the receiving of the prescription order 202 and the entering of corresponding data 205 stages typically occur near the beginning of the work flow 200, and the payment stage 225 typically occurs near the end of the work flow 200. In an embodiment, the stage corresponding to receiving the prescription order 202 is a first stage of the work flow 200, and the payment stage 225 is a last stage of the work flow 200. With the present disclosure, if a pharmaceutical consultation is required or desired, a consultation recording block (e.g., a consultation block) corresponding to the required or desired pharmaceutical consultation, the patient, and the prescribed drug may be generated during any stage 202-225 of the work flow 200.

Figure 3:
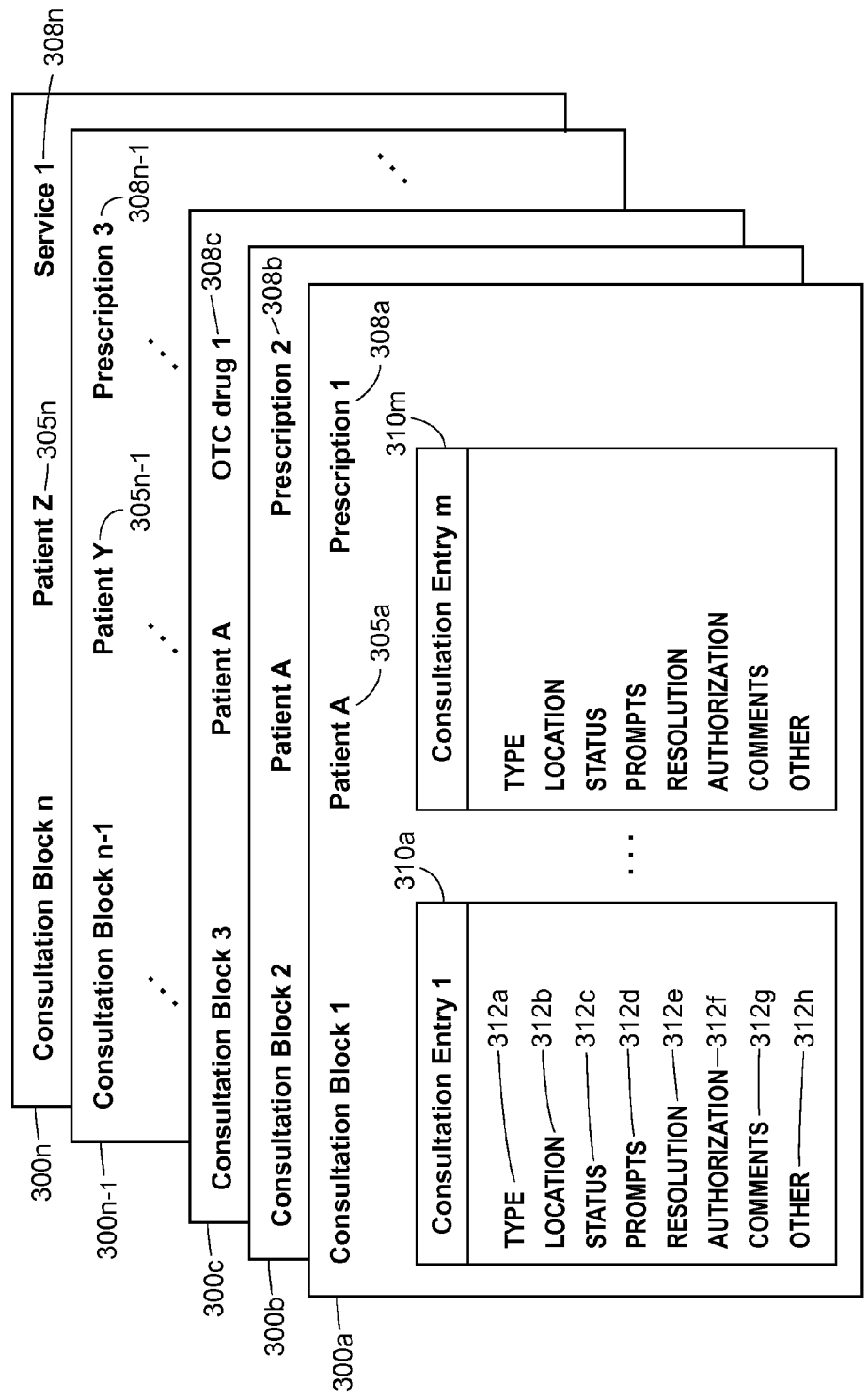
FIG. 3 is a diagram of an example of consultation blocks and consultation entries.
Figure 9:
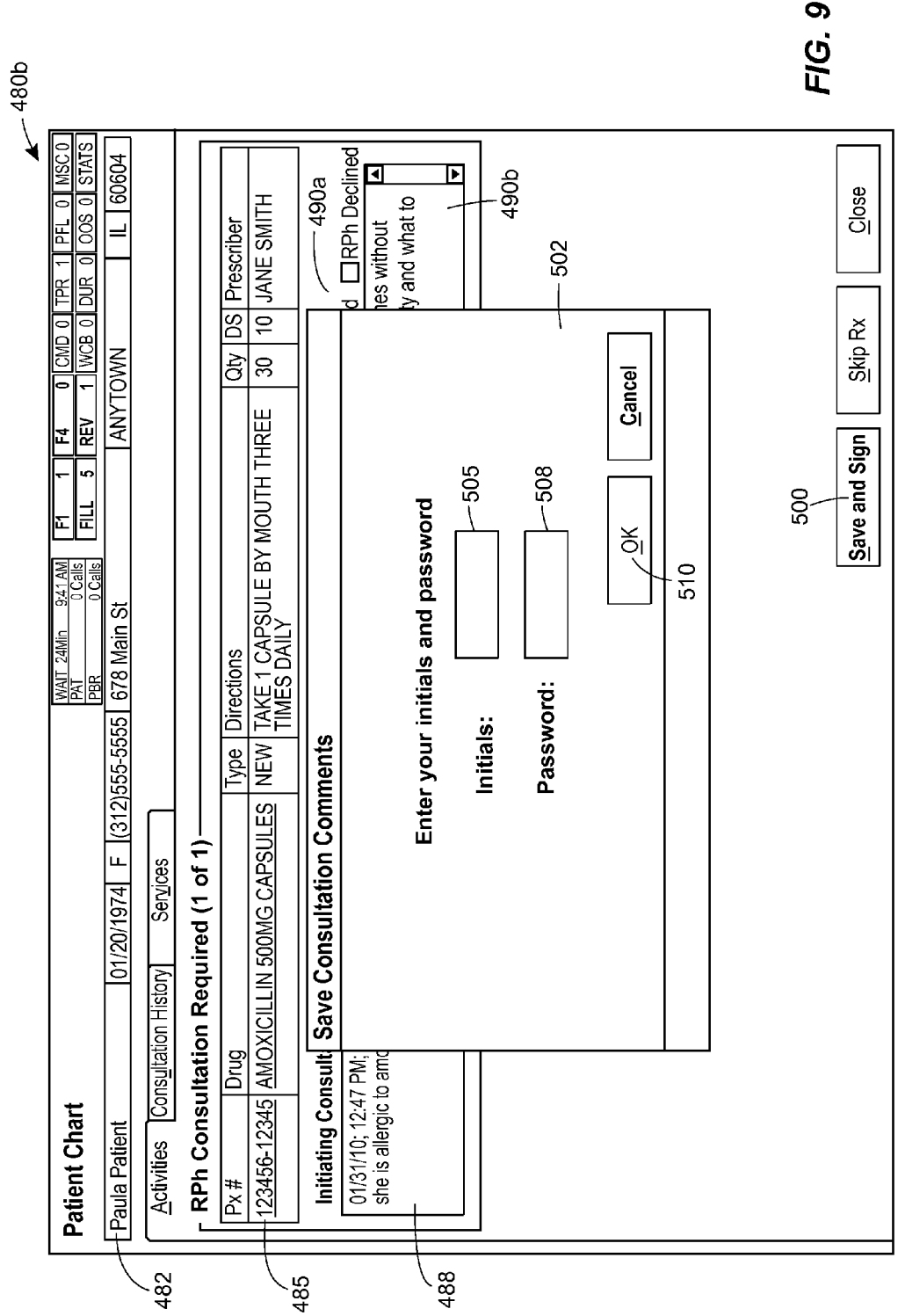

FIG. 3 illustrates an embodiment of a plurality of consultation recording blocks (also referred to herein as "consultation blocks") 300a-300n. The consultation blocks 300a-300n may be generated, for example, by the instructions 40 of FIG. 1, and may operate in conjunction with the system 100 of FIG. 1 or with other suitable systems. In some embodiments, the consultation blocks 300a-300n may be generated by other instructions stored on the memory 8 of the computing device 2. The generated consultation blocks 300a-300n may be stored in a memory that is accessible to the computing device 2, such as data storage entity 28, memory 8, RAM 10, or some other memory that is directly or remotely connected to the computing device 2.

Each consultation recording block 300a-300n may correspond to a particular patient 305a-305n and to a particular product 308a-308n. A product referenced by a consultation block 300a-300n may be, for example, a drug or product prescribed by a prescription order for a respective patient, an over-the-counter (OTC) product (e.g., ibuprofen, hydrocortisone, Vitamin E, etc.), or a service provided by the pharmacy (e.g., a vaccination, a blood pressure reading, etc.). Note that more than one consultation block for a same patient may be possible (e.g., consultation blocks 300a, 300b and 300c). Different consultation blocks for a same patient may correspond to different prescribed drugs (e.g., consultation block 300a for prescription drug 1 indicated by reference 308a, and consultation block 300b for prescription drug 2 indicated by reference 308b), or different consultation blocks for a same patient may correspond to different products (i.e., consultation block 300a for prescription drug 1 indicated by reference 308a, and consultation block 300c for OTC drug 1 indicated by reference 308c). In some embodiments (not illustrated), multiple consultation blocks corresponding to a same patient may be linked. In some embodiments (also not illustrated), a particular consultation block may correspond to a single patient and to multiple products, that is, multiple prescription drugs or products may be referenced by a single consultation block. In some embodiments (also not illustrated), a particular consultation block may correspond to a single patient and to multiple fills (e.g., initial and subsequent re-fills) of a particular prescription order.

Each consultation recording block 300a-300n may include one or more consultation entries. For clarity of illustration, FIG. 3 illustrates only the consultation entries 310a-310m corresponding to the consultation block 300a, however, it is understood that the other consultation recording blocks 300b-300n may also each include any number of respective consultation entries. Each consultation entry 310a-310m may correspond to a different consultation that is associated with the patient 305a and the product 308a as referenced in the consultation block 300a, e.g., to a consultation that is desired or required to occur, a consultation that in process, or to a consultation that has occurred. Each consultation entry 310a-310m may include at least one portion or field (e.g., at least one of fields 312a-312h for entry 310a, and at least one of fields 315a-315h for entry 310m) for recording information associated with the respective consultation. Typically, but not necessarily, a consultation entry 310a-310m may include at least a status field 312c and an authorization field 312f.

In the embodiment illustrated by FIG. 3, the consultation entry 310a may include a type field or portion 312a for indicating a type of consultation. The type of consultation recorded in the type field 312a may correspond to a particular stage during which a consultation occurred (e.g., DUR/clinical review 210, third party validation 220, etc.). The type of consultation may indicate whether the consultation was automatically generated or user requested. For example, a consultation may be automatically generated based on a stage of a work flow or a consultation may be automatically generated based on a rule or guideline, and the impetus for consultation entry generation may be reflected in the type field 312a. Additionally or alternatively, the type of consultation recorded in the field 312a may correspond to a level of legal or industry requirement (e.g., federally required, board of pharmacy required, technician consultation, etc.). Additionally or alternatively, the type of consultation recorded in the field 312a may correspond to a mode of the consultation (e.g., telephone, email, chat, in person, etc.), and/or to a level of authority of a party who is able to clear or authorize the consultation (e.g., clerk, pharmacy technician, registered pharmacist, etc.). Other data corresponding to the type of consultation may be stored in conjunction with the type field 312a. In some embodiments, the indication of the type of consultation stored in the type field 312a may be a code, an abbreviation, or some other indication.

The consultation entry 310a may alternatively or additionally include a location field or portion 312b for indicating a location at which the consultation is to occur, is occurring or has occurred. For example, the location field 312b may indicate a particular pharmacy store front or a particular remotely located pharmacy call center or Internet order center. In some embodiments, the indication of the location stored in the field 312b may be a code, an abbreviation, or some other indication.

The consultation entry 310a may alternatively or additionally include a status field or portion 312c for indicating a status of the consultation and for receiving an indication of a change in the status. The range statuses of the consultation, in one embodiment, may be binary, e.g., "consultation completed" and "awaiting consultation," or similar. Of course, in other embodiments, other additional consultation statuses are possible, such as "consultation performed but not yet authorized." In some embodiments, the indication of the status of the consultation stored in the field 312c may be a code, an abbreviation, or some other indication. In some embodiments, if the status is "consultation performed" or equivalent, other data corresponding to the performed consultation may be stored in conjunction with the status field 312c. For example, a time and an identity of the person performing the consultation may be received and stored in conjunction with the status field 312c. In some embodiments, the status field 312c may be automatically updated based on other fields, e.g., the status field 312c may automatically be updated to "consultation completed" when an authorization for the consultation is recorded.

The consultation entry 310a may alternatively or additionally include a prompts field or portion 312d for displaying a set of prompts corresponding to the consultation. Typically, but not necessarily, the contents of the prompts field 312d may correspond to a stage of a work flow with which the consultation is associated (e.g., the work flow 200), and may automatically be displayed in the consultation entry 310a. The prompts field 312d may include one or more questions to ask during the consultation and/or one or more reminders for the pharmaceutical personnel to perform certain activities. For example, during a DUR stage 210 for the filling of a drug A that is recommended by a DUR board to not be taken with drug B, the prompts field 312d may automatically display "Ask if the patient currently takes drug B?" In another example, during a prescription fill stage 218, the prompts field 312d may automatically display "Are BOTH syringes locked at the appropriate dose?" Other examples of questions and/or reminders may also be possible. The prompts field 312d may include one or more user controls for receiving an acknowledgement to the corresponding question or reminder. In some embodiments, a separate user control may be included for each different prompt or reminder. Acknowledgements may be stored in conjunction with the consultation entry 310a. In some embodiments, progression of the prescription fill through the work flow may be blocked or ceased until one or more acknowledgements are received.

The consultation entry 310a may alternatively or additionally include a resolution field or portion 312e for receiving, recording and displaying a resolution corresponding to the consultation. The resolution of the consultation, in one embodiment, may be one of a range of resolutions including "not occurred," "occurred—patient declined," "occurred—pharmacist declined," "occurred—physician declined," and "occurred—accepted." Of course, in other embodiments, other ranges of resolutions may be possible. In some embodiments, the indication of the resolution of the consultation stored in the field 312e may be a code, an abbreviation, or some other indication. In some embodiments, other data corresponding to the resolution of the consultation may be stored in conjunction with the status field 312e. For example, a date and time of the resolution and an identity of the person resolving the consultation may be received and stored in conjunction with the resolution field 312e. In some embodiments, additional comments (e.g., character strings entered by a user) may be included in the resolution field 312e.

The consultation entry 310a may alternatively or additionally include an authorization field or portion 312f for receiving, recording and displaying an authorization corresponding to the consultation. In an embodiment, the authorization field 312f may receive and store an indication of an authorizing party of the consultation. The authorization may be received by any known means of authorization, including (but not limited to): electronic identification via a secured login, e-signature, bar code, RFID (Radio Frequency Identification) or equivalent, biometric identification, recording of a verbal authorization in conjunction with a recording party's identity, and the like. In some embodiments, other data corresponding to the authorization may be stored in conjunction with the authorization field 312f. For example, a time and date of the authorization may be received and stored in conjunction with the authorization field 312f. In some embodiments, the indication of the authorization stored in the field 312f may be a code, an abbreviation, or some other indication. In some embodiments, additional comments (e.g., character strings entered by a user) may be included in the authorization field 312f.

The consultation entry 310a may alternatively or additionally include a comments field or portion 312g for receiving, recording and displaying one or more comments corresponding to the consultation. Generally, the comments field 312g may allow a user to enter comments (in some embodiments, a maximum pre-determined number of characters) that are pertinent to the consultation. In some cases, the comments may include notes, questions or reminders to be viewed by another pharmaceutical personnel who may access the consultation entry 310a at a later time. For example, a user may enter "Please check if patient is allergic to amoxicillin as profile states cephalexin allergy," or "Patient asked about side effects and interaction with OTC drugs." In some embodiments, other data corresponding to the performed consultation may be stored in conjunction with the comments field 312g. For example, a time and an identity of the person entering the comments may be received and stored in conjunction with the comments field 312g.

Of course, one or more other fields or portions 312h to receive, record and display other information corresponding to a consultation may be alternatively or additionally included in the consultation entry 310a. Similar to the fields 312a-312g, the one or more other fields 312h may be manually or automatically generated, and may be stored in conjunction with the consultation entry 310a.

In some embodiments, some part of one or more of the fields 312a-312h may be automatically populated or filled, either partially or completely, by a character string or other indication (e.g., "auto-populated" or "auto-filled"). For example, if the consultation entry 310a is accessed under a particular pharmacist's login, an indication of that particular pharmacist's identification may be automatically populated into any field in which the pharmacist enters input, such as in the resolution field 312e, the comments field 312g or the authorization field 312f. In another example, a time/date of input entry may be automatically recorded in conjunction with some or all of the fields 312a-312h. In yet another example, a particular field may present several auto-filled character strings for selection (e.g., selectable codes or phrases corresponding to a range of resolution statuses in the resolution field 312e). Other examples and uses of one or more auto-filled character strings (user-selectable, not user-selectable or some combination of the two) in any of the fields 312a-312h may be possible.

FIGS. 4 through 14 and FIGS. 15A-15C each illustrates an example screen shot of an example user interface screen that may be displayed in conjunction with a pharmaceutical enterprise computing system. In some embodiments, each of the screen shots illustrated in FIGS. 4-15C may be displayed in conjunction with embodiments of the system 100 of FIG. 1, the workflow 200 of FIG. 2, the consultation blocks 300 of FIG. 3, or in conjunction with other suitable systems, workflows and/or consultation blocks. Each of the screen shots illustrated in FIGS. 4-15C may be displayed in conjunction with embodiments of the method 700 (to be discussed in a later section with respect to FIG. 16 in a later section), the method 800 (to be discussed with respect to FIG. 17 in another later section), or other suitable methods. Furthermore, each of the screen shots depicted in FIGS. 4-15C is not limited to only the fields and or user controls illustrated thereon. In some embodiments, one or more illustrated fields and/or user controls may be omitted from a particular user interface screen, and in some embodiments, one or more other fields and/or user controls that are not illustrated may alternatively or additionally be included on a particular user interface screen.

Figure 4:
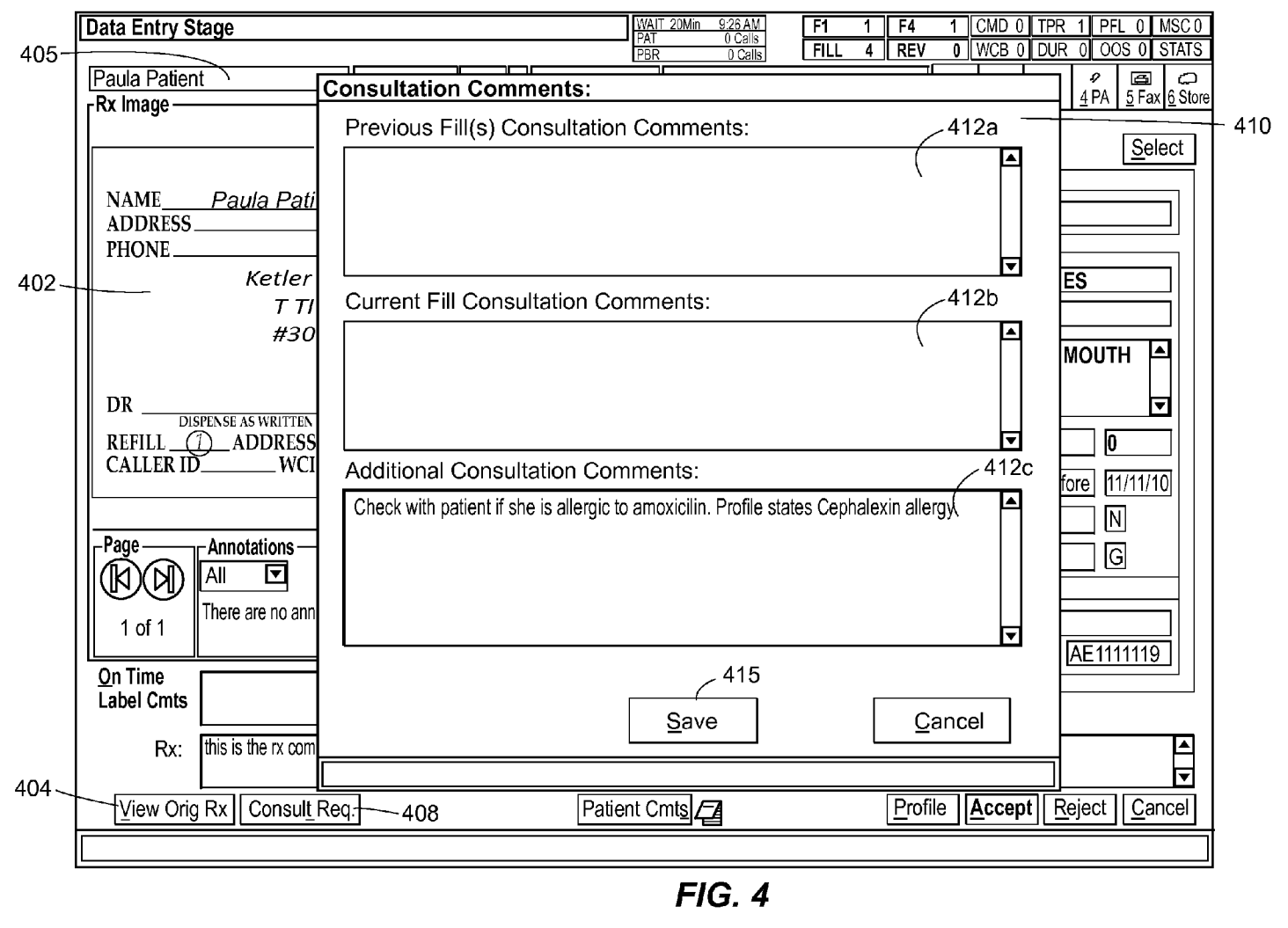

FIG. 4 illustrates a screen shot 400 of an example user interface screen presented during a data entry stage of a work flow for filling a prescription order, such as the data entry stage 205 of FIG. 2. The screen shot 400 may include a scanned image of the original prescription order 402 or other representation of the original prescription order. In an embodiment, the scanned image of the prescription order 402 may have been displayed upon a user request, such as a user activation of a "View Original Rx" button 404. The screen shot 400 may include an indication of the patient 405 (e.g., "Paula Patient") for which the original prescription order was prescribed. In the scenario of FIG. 4, a pharmacist or other pharmaceutical personnel has blocked the progression of the work flow at this data review stage by clicking on the "consultation required" button or user control 408. That is, the progression of the work flow, as tracked by the pharmaceutical consultation computing system on which the screen shot 400 is displayed, may not proceed until at least some portion of a consultation is recorded. In response to the activation of the button 408, a pop-up window 410 has appeared. The contents of the pop-up window may reflect a corresponding consultation recording block for Paula Patient and its respective consultation entries 412a, 412b, 412c. In this scenario, no previous consultations corresponding to a previous fill or to the fill at hand have been requested or performed, so consultation entries 412a and 412b are blank. The user has entered new comments into consultation 412c "Check with patient if he is allergic to amoxicillin. Profile states Cephalexin allergy," and upon activation of the "Save" button 415, the new comments may be saved into the consultation entry 412c, and the work flow may proceed. In an embodiment, the characters entered into the consultation entry 412c may be saved in a comments field of the consultation entry 412c (such as comments field 312g).

Figure 5:
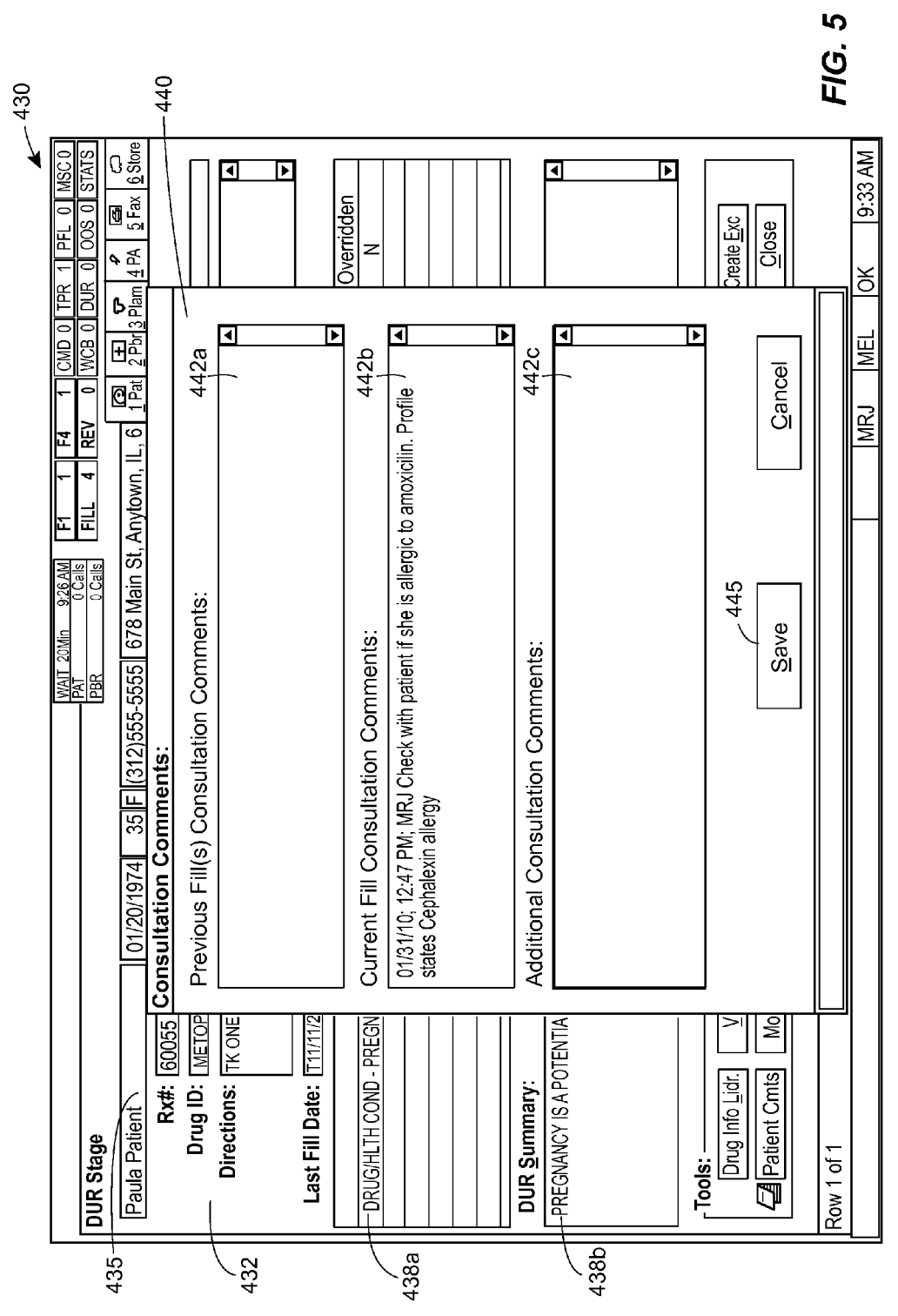

FIG. 5 continues the work flow of FIG. 4, and illustrates a screen shot 430 of an example user interface screen presented during a subsequently occurring DUR stage, such as the DUR stage 210. The screen shot 430 may display details of the entered prescription order 432, patient information 435, and DUR information 438a and 438b. In an embodiment, the DUR information 438a and 438b may have been automatically displayed, based on information in the entered prescription order 432, when the screen shot 430 was presented. A "consultation" button on the screen 430 (not visible, as it is obscured) has been activated, and, based on the activation of the consultation button, a pop-up window 440 has appeared. The contents of the pop-up window 440 may reflect the corresponding consultation block from FIG. 4 and its respective consultation entries 442a, 442b, 442c. In screen shot 430, however, the previously entered consultation entry (i.e., field 412c of FIG. 4) has already been saved, so its contents now appear in the field 442b. Thus, any previous consultation comments entered upstream in the work flow may be identified and displayed in subsequent views of a consultation block. At this point in the scenario, the user may enter any additional comments into the field 442c, and upon activation of the "Save" button 445, the additional comments 442c may be saved into a corresponding new consultation entry of the consultation block. Note that the user who interacts with the screen 400 of FIG. 4 and the user who interacts with the screen 430 of FIG. 5 may be a same user, or they may be different users accessing the consultation block via different computing devices. In some cases, the users may even be at different locations and still be able to view and interact with a same consultation block.

FIG. 6 illustrates an example of a screen shot 460 of an example user interface screen that is not associated with any particular stage of a work flow for filling a particular prescription order. The screen shot 460 may include a list of prescription orders 462 that are currently pending or being processed in a work queue 465 of a pharmacy location. Summary parameters of each prescription order in the work queue 465 (e.g., status, e-pay, bin, type, promised time, patient, etc.) may be displayed. In particular, a "consultation required?" field 468 may be displayed for each prescription order. In the embodiment illustrated in FIG. 6, a "Yes" in the field 468 may indicate that a consultation authorization is outstanding for a respective prescription order, but in other embodiments, other wording and indications may be used (e.g., the character string "consultation authorized?" may be displayed as a header for the field 468, and a "Yes" entered into the field 468 may indicate that a consultation authorization has been completed for the respective prescription order.)

In the screen shot 460, a user has selected Paula Patient's prescription order for amoxicillin based on the value of the field 468 indicating that a consultation is outstanding. After Paula Patient's prescription order is selected, the user may activate a "consultation" button 470, and access to the consultation block for Paula Patient's amoxicillin prescription order may be provided, as shown in a screen shot 480a illustrated in FIG. 7.

In FIG. 7, the screen shot 480a of an example user interface screen displays the contents of the consultation block corresponding to Paula Patient's amoxicillin prescription order from the screen 460 of FIG. 6. The screen shot 480 may include an indication of the patient 482 and an indication of the prescription order 485. Comments that were previously entered at some earlier stage of the work flow for this prescription order may be displayed 488. Resolution fields 490a and 490b may also be displayed. In this embodiment, the resolution fields 490a and 490b may include one or more check boxes 490a to indicate a status of a resolution and a character entry field 490b to include any free-form comments corresponding to the resolution. In some embodiments, in addition or alternative to free-form comments, the field 490a may display a group of pre-determined comments for user selection. In some embodiments, the resolution fields 490a and 490b may correspond to a resolution portion 312e of a consultation entry, and, in some embodiments, at least a part of the check boxes 490a may be included in a status portion 312c of the consultation entry.

In a scenario where the user desires to enter free form resolution comments into the resolution field 490b, FIG. 8 depicts a screen shot 480b of the example user interface screen 480a after the user has entered the free form resolution comments into the field 490b and has checked the appropriate box 490a. The consultation is now complete, save for an authorization. A user selection of the "Save and Sign" button 500 may bring up an authorization screen, such as the pop-up authorization window 502 shown in FIG. 9. The authorization window 502 of FIG. 9 may include a login field 505 and a password field 508, or some other secure authorization means. After the user has entered his or her identification into fields 505 and 508, the authorization of the consultation may be completed and saved into the consultation entry by activation of the button 510. Thus, at this point, a refreshing of the work queue screen 460 of FIG. 6 would show that Paula Patient's amoxicillin prescription order may have a value of "No" in the "consultation outstanding?" field 468.

In the scenario where the user does not desire to enter free form comments into the resolution field 490b of FIG. 7, FIG. 10 depicts the screen shot 480a of FIG. 7 after the user has selected the "consultation completed" check box 490a. Based on the selection of the check box 490a, a character string "Consultation Completed" may be auto-filled into the resolution comments field 490b. Upon user selection of the "Save and Sign" button 500, authorization may proceed as previously discussed above.

FIGS. 4-10 have illustrated examples of user requested consultations during various stages of a work flow of filling a prescription order. FIGS. 11 and 12 illustrate examples of automatically generated consultations.

For example, FIG. 11 depicts a screen shot 530 of an exemplary, automatically generated user interface consultation screen that corresponds to a required consultation for a DUR review stage, such as the DUR review stage 210 of the work flow 200. The consultation screen shot 530 (or indication thereof) may be automatically displayed in conjunction with a display of a DUR review stage user interface screen in a pop-up window or similar. For example, the screen shot 530 may be automatically displayed upon entry into the DUR stage 210, or just before exit out of the DUR stage 210. The screen shot 530 may include information corresponding to the patient 532 and information corresponding to drug of the prescription order 535. If any consultation entries were previously entered prior to the DUR stage, they may be displayed (e.g., reference 538).

In an additional field 540 of the consultation screen 530, information corresponding to the DUR stage may be displayed. In an embodiment, the additional field 540 may correspond to a prompts field 312d of a corresponding consultation entry. The information displayed in the field 540 may be based on data corresponding to the stage of the work flow, in this example, the DUR stage 210. In FIG. 11, the DUR review stage may have detected a condition based on the patient information 532, the prescribed drug information 535, an upstream consultation's comments 538, and information stored in a DUR database, and accordingly, the field 540 may be pre-populated or auto-filled with the appropriate prompt(s). The DUR database from which DUR information is gleaned may be, for example, a DUR database generated by information from a pharmacy board or other legal entity, and may be included at least partially in the database 28. In some embodiments, the DUR database may be communicatively connected to the pharmacy consultation computing system with which the screen shot 530 is displayed.

In FIG. 11, the DUR review stage may have determined that a potential issue between a drug that is currently being taken by the patient (e.g., warfarin) and the drug being prescribed by the pending prescription order (e.g., amoxicillin) may be of concern. Based on the determined potential issue, the required consultation screen 530 may be automatically generated and displayed, and the field 540 may be auto-populated with the information corresponding to the potential issue. In this manner, the user may be automatically warned of the potential DUR issue, and a consultation entry may be automatically displayed for resolution. In some embodiments, progression of the work flow of the filling of the prescription drug 535 (as tracked by the pharmaceutical consultation computing system on which the screen shot 530 is displayed) may not proceed until at least some portion of the consultation is resolved and thusly indicated in the fields 545a and 545b. Consultation resolution may proceed in a manner similar to as previously discussed, or in a different manner. Thus, auto-generating consultation entries to highlight or to warn the user of any potential issues at each work flow stage may ensure compliance with consultation requirements and may optimize patient protection.

Of course, for stages of a work flow other than the DUR review stage, one or more databases other than the DUR database (e.g., a clinical review database, a patient information database, etc.) and that corresponds to the work flow may be accessed to determine whether or not a consultation entry should be automatically generated. One or more fields in the screen 530 may be auto-populated based on the other database(s). In some scenarios, automatic generation of a consultation may not be based on database information corresponding particularly to a work flow stage, but may be additionally or alternatively based on factors such as company policy, insurance requirements, customer service criteria, or others.

Turning now to FIG. 12, the methods and systems of the present disclosure also may provide checklists or other prompts to aid pharmaceutical personnel in filling prescription orders. FIG. 12 is an example screen shot 560 of an exemplary user interface consultation screen that was automatically generated and displayed upon entry into or just prior to exit from a prescription fill stage, such as the prescription fill stage 218 of the work flow 200. The screen shot 560 may include information corresponding to the patient 562 and information corresponding to drug of the prescription order 565. If any consultation entries were previously entered prior to the prescription fill stage, they may be displayed in a field 568. In an additional field 570, a checklist corresponding to the prescribed drug 565 may be displayed. In an embodiment, the field 570 may correspond to the prompts field 312d of a corresponding consultation entry.

The checklist displayed in the field 570 may include a list of physical preparation activities that are required to be performed during the prescription fill stage. The contents that are auto-populated into the field 570 may be based on the patient 562, the information in some part of the prescription order 565, previous consultation comments 568, or information from another database, such as a database storing best practices information or a database including company policy information. In this embodiment, only upon user acknowledgement of the displayed prompts (e.g., checking "Yes" for each item in the checklist 570) may the user be able to enter data into the resolution field 572, but in other cases, such stringent measures may not be desired. At this point of the work flow, the user has checked off each item in the field 570, and has indicated completion of the consultation in the field 572. The user may click the "Save and Sign" control 575 to proceed with authorization, in a manner such as previously discussed. Thus, by automatically generating and automatically populating prompts corresponding to a particular work flow stage, actions taken by pharmaceutical personnel at the particular work flow stage may be more accurate and complete. Of course, the prompts displayed in the field 570 are not limited to being only displayed during the prescription filling stage. One or more different prompts in the additional field 570 may be automatically displayed in conjunction with other stages of a work flow for filling a prescription. Furthermore, in some embodiments, a user acknowledgement of the displayed prompts may not be required.

Figure 13:
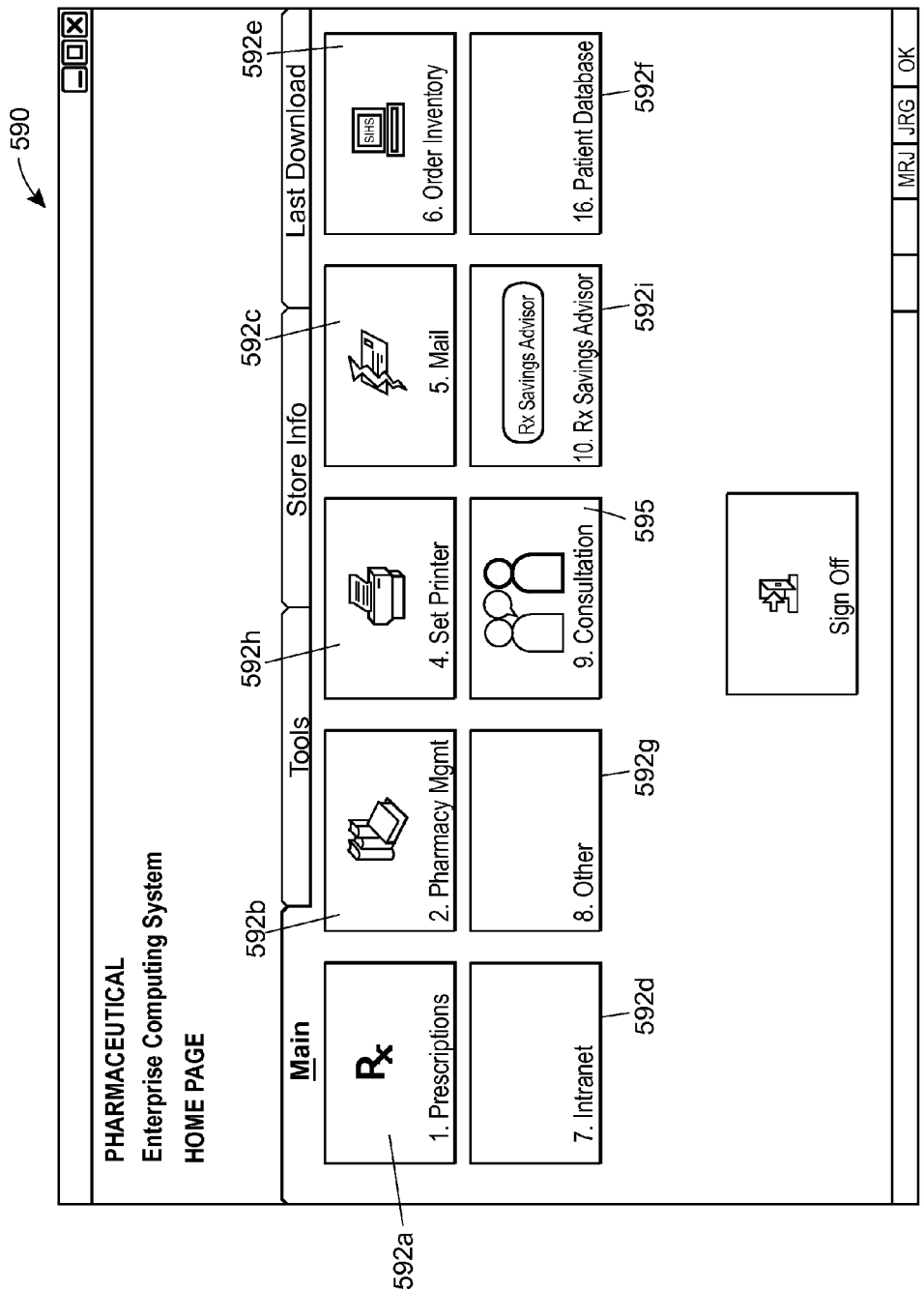

FIG. 13 illustrates an example of a screen shot 590 of another user interface screen that is not associated with a particular stage of a work flow for filling a prescription order. In particular, screen shot 590 may be a home or main page in a pharmaceutical enterprise computing system. The screen shot 590 may include user controls to access various parts of the pharmaceutical enterprise computing system, including but not limited to at least one of: a user control for accessing work flows for filling or dispensing prescriptions 592a, a user control for managing administrative tasks such as personnel records, scheduling, etc. at the pharmacy location 592b, a user control for accessing email capabilities 592c, a user control for accessing an enterprise intranet or other private network to which other pharmacy locations of the pharmaceutical enterprise are connected 592d, a user control for ordering and managing inventory 592e, a control for accessing a patient database 592f, a printer access control 592h, a control for accessing third party information (e.g., Medicare, insurance plans, etc.) 592i, or some other user control 592g. In some embodiments, the patient database access 592f may be included in the prescription dispensation control 592a.

The screen shot 590 may also include a consultation user control 595 for providing access to consultation recording blocks. Upon activation of the control 595, a user may be able to create a consultation block or consultation entry, view a consultation block or consultation entry, modify a consultation block or consultation entry, search all available consultation blocks or entries, and/or perform other activities corresponding to consultation blocks, entries, and data corresponding thereto.

Figure 14:
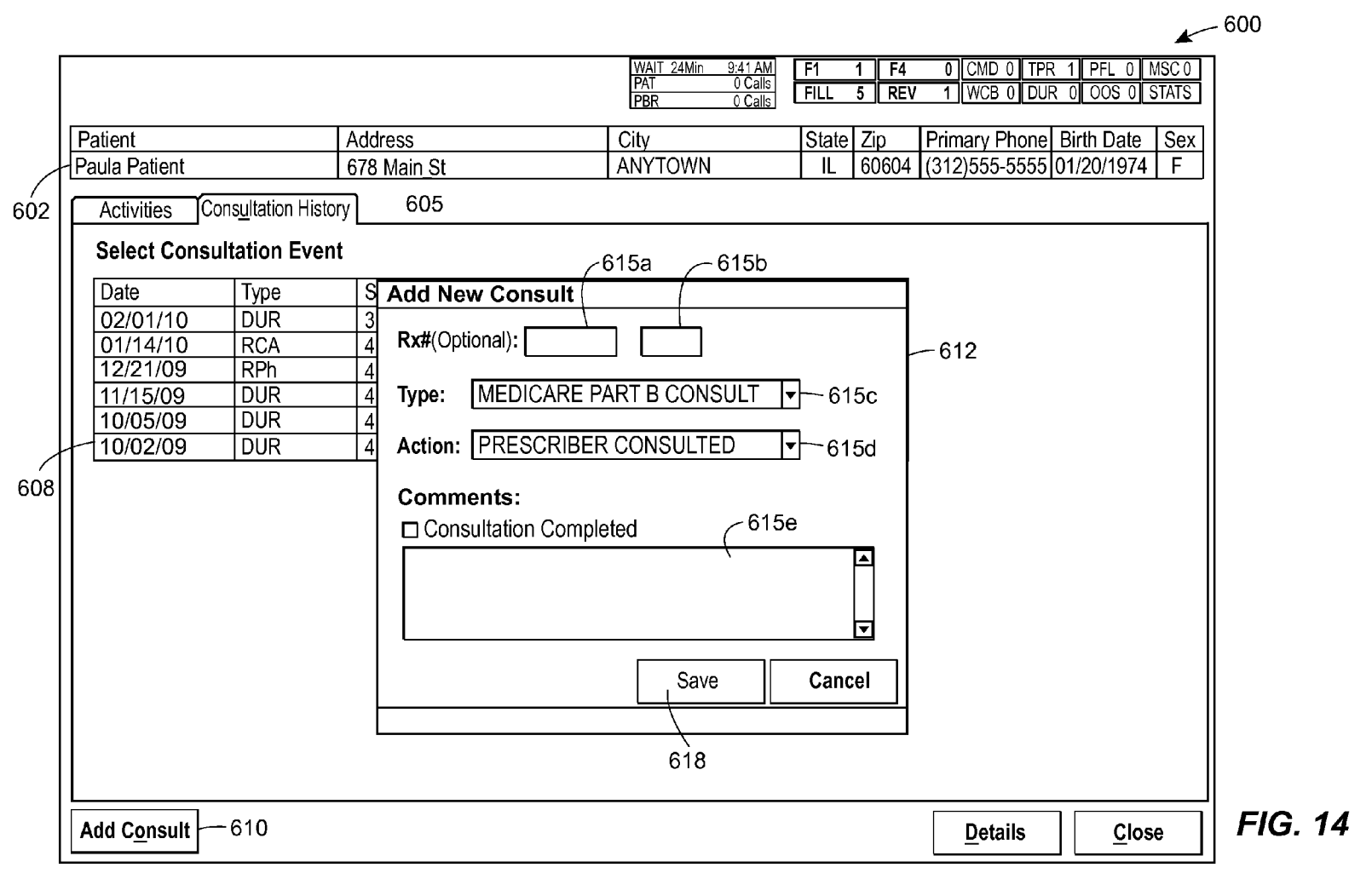

FIG. 14 illustrates an example of a screen shot 600 ultimately resulting from the activation of the "Patient Database" control 592f on the home page 590. Upon activation of the control 592f, a patient database view (not illustrated) may be displayed, and the user may be able to search for and select a particular patient who has been serviced by the pharmaceutical enterprise. From a page or screen corresponding to the particular patient, by activating a "consultation" control or similar, the user may be able to access consultation data corresponding to the particular patient (e.g., create, view, modify, or search consultation blocks or entries corresponding to the particular patient). In particular, FIG. 14 depicts an embodiment of a patient consultation summary page 600 that may have resulted from a first selection of the patient 602 from a list of patients (not shown) accessed via the "Patient Database" control 592f on the home page 590, and then a second selection of a "consultation" control (not shown). The selected patient page 600 includes an indication of the patient 602 and a consultation history tab 605 for accessing all historical consultation blocks corresponding to the patient. Clicking on the consultation history tab 605 has resulted in a summary 608 of the consultation blocks (or in some embodiments, of the consultation entries) corresponding to the patient 602. On FIG. 14, the user has selected the "Add Consult" button 610, which has resulted in the appearance of a pop-up window 612 for entering information for a new consultation block. The user may enter or select data to populate one or more fields 615a-615e of a new consultation entry of the new consultation block, and may save the consultation by activating the "Save" button 618. Of particular note in FIG. 14, the illustrated new consultation entry 612 does not correspond to a product vended by the pharmaceutical enterprise. Rather, the new consultation entry 612, as indicated by the value of the consultation type 615c, corresponds to a discussion about Medicare Part B between the patient (or his or her representative) and the pharmaceutical personnel. Indeed, a consultation entry need not correspond to a prescribed product but instead may correspond to a service (fee based or not fee based) such as discussing Medicare or other third party provider benefits, providing advice on OTC drug interactions, administering a flu or pneumonia shot, taking a blood pressure reading, or other services.

On user interface screens other than a home page (e.g., screen 590 of FIG. 13) that are not associated with any particular stage of a work flow, if one or more consultation blocks or entries are available but not displayed, an indicator may be displayed that alerts the user to the presence of the one or more available consultation blocks. For example, a flag or other graphical indicator may be displayed, or a character string on a tool-bar or drop down menu may be displayed. Upon clicking the indicator, a user may be provided access to the one or more consultation blocks.

Thus, in general, consultation recording blocks or consultation blocks may be able to be accessed via any user interface screen of a pharmaceutical enterprise computing system, whether the user interface screen is work flow related or not. The aggregation of consultation blocks in an accessible memory (e.g., the data storage entity 28, the memory 8, the RAM 10, or some other memory that is directly or remotely connected to the computing device 2) may allow for quick and effective access to consultation data. Furthermore, the aggregation of consultation blocks also may allow for quick and effective determination of compliance (or non-compliance, as the case may be) of pharmaceutical consultations to legal, enterprise and other requirements. FIGS. 15A-15C illustrate example screen shots corresponding to such consultation compliances.

FIG. 15A depicts an example audit report 630 for a Board of Pharmacy Inspection based on the consultation blocks of the present disclosure. The audit report 630 may correspond to a particular prescription fill for a particular patient. In this example, the audit report 630 corresponds to a fill of allopurinol 100 mg tablets on Oct. 21, 2009 for Paula Patient. The audit report 630 may include typically reported information such as patient information 632, drug information 635, prescriber information 638, fill work flow history 640, and DUR review information 642. The audit report 630 may also include information regarding consultations 645. Details of the consultation information 645 included on the audit report 630 are more fully detailed in FIG. 15B.

Turning to FIG. 15B, the consultation information 645 of the audit report 630 may include a history of all consultation entries corresponding to the particular fill. In an embodiment, some or all of the contents of the consultations entries of the consultation block corresponding to the particular fill may be indicated or entirely included in the consultation information 645. In the example illustrated in FIG. 15B, two consultations (648 and 650) were held in conjunction with Paula Patient's Oct. 21, 2009 fill of allopurinol 100 mg tablets. A record of the first consultation 648 indicates that it was manually initiated during a product review stage by registered pharmacist (RPh) M. R. Johnson, and was authorized by registered pharmacist P. T. Pill. A record of a second consultation 650 indicates that it was automatically generated, and was authorized by the registered pharmacist P. T. Pill. Each of the consultation records 648 and 650 may include information from the status field 312*c*, the comments field 312*g*, the type field 312*a*, the location field 312*b*, the resolution field 312*e*, and the authorization field 312*f* of their respective consultation entries. Of course, the format and contents of the audit report 630 are exemplary. Other embodiments of the audit report 630 may omit, add, or modify the illustrated format and contents.

FIG. 15C depicts a consultation compliance search and report 670 that has a wider perspective than the audit report 630. While the audit report 630 provided information pertaining to a single prescription fill, the consultation compliance report 670 may provide aggregated information across multiple prescription fills. The consultation compliance report 670 may provide aggregate information in at least one of multiple views, such as by pharmacy location, by consultation type, by resolution type, or by authorizing party. Indeed, the consultation compliance report 670 may provide aggregate information based on any number or combination of the fields 312*a*-312*h* of consultation blocks, consultation entries, and/or their values. In the particular example depicted in FIG. 15B, the compliance report 670 was generated based on a request 672 for all pharmaceutical personnel-requested consultations that were patient declined at pharmacy location #88888 between Jan. 1, 2007 through Mar. 31, 2007 (e.g., fields 675*a*-675*d*). The resultant compliance report 670 may include a listing of consultation entries that meet the selected criteria 675*a*-675*d*. A summary of information 678*a*-678*e* for each consultation entry may be included in the compliance report 670, and may include information from one or more of the fields 312*a*-312*h*, in an embodiment. In some embodiments, the information included in the summary set of information 678*a*-678*e* and/or the fields 312*a*-312*h* may be selectable. Of course, the request 672 is not limited to being based on the illustrated search parameters 675*a*-675*d*, nor is the generated consultation compliance report 670 limited to displaying the fields 678*a*-678*e*. Other request parameters and other fields may be possible. This flexibility and aggregation of consultation block data allows a pharmaceutical enterprise to easily audit and review pharmaceutical consultation compliance at varying levels and viewpoints to help the pharmaceutical enterprise to make better management decisions. For example, with aggregated consultation blocks, a pharmaceutical enterprise may determine that a particular location has an abnormally high rate of patient declined resolutions, and may drill further down in the consultation data to determine if the abnormally high rate is attributable to a particular pharmaceutical enterprise employee. In another example, a pharmaceutical enterprise may be able to determine if there is a relationship between higher numbers of manually generated consultations and higher customer satisfactions scores. Other examples may be possible.

Figure 16:
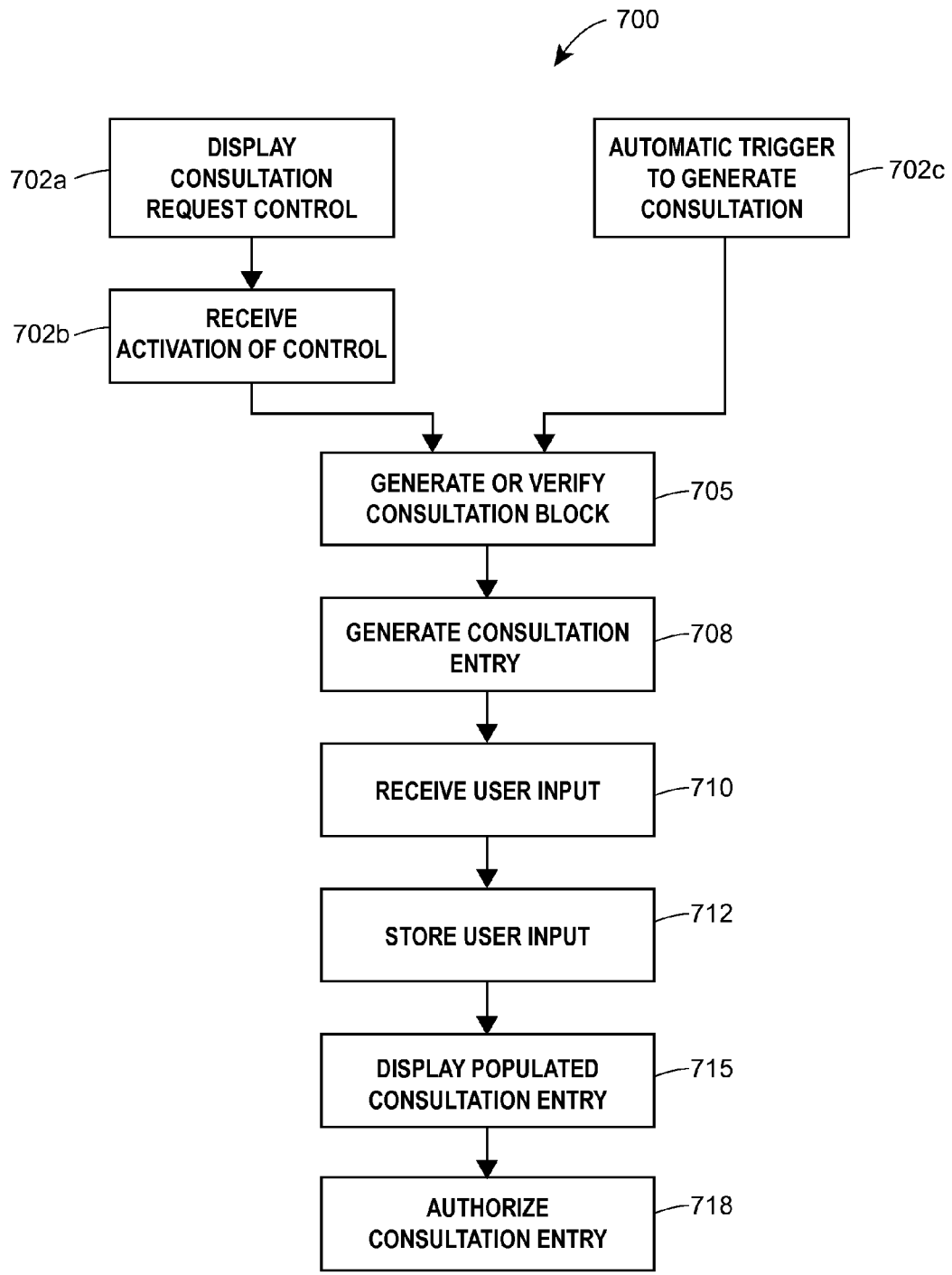
FIG. 16 depicts an example method providing comprehensive pharmaceutical consultations.

FIG. 16 depicts an example method 700 of generating a consultation entry corresponding to a pharmaceutical consultation for providing comprehensive pharmaceutical consultations. The method 700 may operate in conjunction with embodiments of the system 100 of FIG. 1, the workflow 200 of FIG. 2, and/or the consultation blocks 300 of FIG. 3, or the method 700 may operate in conjunction with other suitable systems, workflows and/or consultation blocks. The method 700 may operate with any or all of embodiments of the user interface screens depicted in FIGS. 4-15C.

At a block 702*a* of the method 700, a consultation request button or user-activated control may be displayed on a screen of a display device. In some embodiments, the control may be displayed on a screen that corresponds to a particular stage of a work flow for filling a prescription order at a pharmaceutical enterprise (e.g., as shown in FIG. 4, 5, 11, or 12). The particular stage of the work flow may be any stage of the work flow 200 illustrated in FIG. 2 or another stage. In fact, the control may be displayed on any or all screens corresponding to at least one particular work flow stage. In other embodiments, the control may be displayed on a screen that does not correspond to any work flow stage (e.g., as shown in FIG. 6 or FIG. 13). At a block 702*b*, an indication of an activation of the button or control displayed at the block 702a may be received, and at a block 705, a consultation block may be generated based on the user activation of the control, if one does not already exist for the patient.

In some embodiments, an automatic trigger to generate a consultation request may be received (block 702c). The trigger may be automatically generated based on any number of factors, such as when a particular stage of a work flow is entered into or exited from, or when a particular type of consultation is required per legal, industry, enterprise or local requirement. At the block 705, a consultation block may be generated based on the automatic trigger, if one does not already exist for the patient.

At the block 705, in situations where a consultation block has already been generated some time prior to the blocks 702a or 702c (for instance, if a prior consultation for the patient and the product previously occurred, if consultation comments were previously entered, etc.), the block 705 may merely verify the existence of the consultation block.

At a block 708, a consultation entry in the consultation block may be generated in response to the request received at the block 702b or the trigger received at the block 702c, as the case may be. The consultation entry may include one or more fields to receive information corresponding to a particular consultation, such as one or more of the fields 312a-312h of FIG. 3. One or more of the fields 312a-312h may be automatically generated for inclusion in the consultation entry upon the generation of the consultation entry. Alternatively or additionally, one or more of the fields 312a-312h may be added to the generated consultation entry per a user request. In some embodiments, some or all of the contents of one or more of the fields 312a-312h may be auto-filled or populated. Typically, but not necessarily, some or all of the fields of the consultation entry may be displayed or otherwise presented on a display device.

At a block 710, user input corresponding to the consultation entry may be received. The user input may be received by any known user input interface, such as a user activation or selection of a control, keyboard strokes or mouse movement, touch screen, voice activation, etc., and the received user input may populate one or more of the fields 312a-312h. At a block 712, the received user input may be stored in conjunction with the consultation entry. In some embodiments, an optional block 715 may include displaying the consultation entry including displaying any populated fields 312a-312h.

At a block 718, the consultation entry may be authorized by a user or party that has an appropriate level of authorization for the consultation entry. For example, a registered pharmacist may be permitted to authorize any type of consultation, a pharmaceutical enterprise technician may not be permitted to authorize DUR stage consultations but may be permitted to authorize consultations corresponding to all other work flow stages, and a pharmaceutical clerk may be permitted to authorize certain types of consultations, such as recording verbally relayed patient information or verifying third party coverage. In some embodiments, the level of authorization may be indicated by a login or other securitized access (e.g., bar code swipe, initials, password, biometric identification, etc.) to the consultation block and/or to the pharmaceutical consultation system in which the consultation block is stored. In some embodiments, different consultation entries may each be authorized by different pharmaceutical personnel. In some embodiments, multiple consultation entries may be authorized with a single authorization action. In some embodiments, different consultation entries may be authorized at different stages of a prescription order filling work flow.

In some embodiments, some or all of the blocks of the method 700 itself may be executed by different pharmaceutical personnel at different stages of the prescription order filling work flow, and some blocks may even be repeated. For example, a technician may receive a prescription order at a local pharmacy store front, enter corresponding data, and activate a consultation request button (block 702b) to record (blocks 710 and 712) verbally relayed information during the prescription drop-off. At some later time, a remotely located licensed pharmacist, whose duties include calling a list of patients who require licensed pharmaceutical consultations, may open and display the consultation block (block 715), read the information recorded by the technician, and call the patient to conduct a DUR consultation. The remotely located pharmacist may then record the DUR consultation (blocks 710 and 712) in another consultation entry of the consultation block. Finally, prior to prescription pickup, a locally located pharmacist may open and display the consultation block (block 715), verify contents of all consultation entries, and click a single button to authorize all of the consultation entries at one time (block 718). Of course, other examples of different entities performing different blocks of the method 700 may also be possible.

Thus, using embodiments of the method 700, pharmaceutical consultations for a particular prescription fill (and in some cases, for the particular prescription fill and its re-fills) may all conveniently be consolidated into a single consultation block. With the single consultation block, consultation entries, tracking, resolutions, authorizations, and other tasks of pharmacists and non-pharmacist personnel may be tracked across time and across different personnel to ensure comprehensive pharmaceutical consultations. Accordingly, the singular responsibility of a pharmacist to remember and record all desired or required consultations during the product review or payment stage of a prescription fill is mitigated. The systems and techniques as disclosed herein may allow consultation information to be entered and recorded during any stage of the work flow by any pharmaceutical personnel, so the chance of an inadvertent omission is lessened. Furthermore, the systems and techniques as disclosed herein may prompt or remind pharmaceutical personnel to perform consultations at critical stages of the prescription fill. In some embodiments, the prescription fill may even be blocked from proceeding until consultations are performed and/or recorded. In this manner, comprehensive pharmaceutical consultations are able to be more easily achieved.

In some embodiments, multiple instances of the method 700 may be executed. For example, a different instance of the method 700 may be executed for each different consultation that is performed or is desired to be performed for a particular patient and prescription order. Different instances of the method 700 may be performed to generate multiple consultation blocks corresponding to multiple patients.

Figure 17:
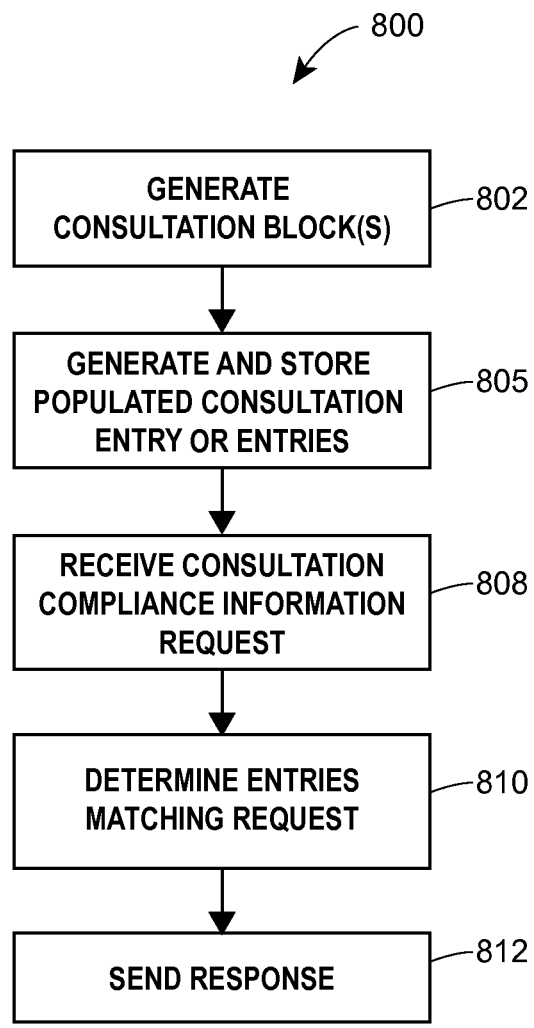
FIG. 17 depicts an example method for providing pharmaceutical consultation compliance.

Turning to FIG. 17, an example method 800 for providing pharmaceutical consultation compliance is depicted. The method 800 may operate in conjunction with embodiments of the system 100 of FIG. 1, the workflow 200 of FIG. 2, and/or the consultation blocks 300 of FIG. 3, or may operate in conjunction with other suitable systems, workflows and/or consultation blocks. The method 800 may operate with any or all of the user interface screens depicted in FIGS. 4-15C, and the method 800 may operate in conjunction with embodiments of the method 700 of FIG. 16 and with other suitable methods.

At a block 802, one or more consultation blocks may be generated. The one or more consultation blocks may be generated, in an example, by executing multiple instances of the method 700. Each consultation block may correspond to a particular patient and to a particular product provided by a pharmaceutical enterprise, such as a prescription order, an OTC drug or product, or a service. Each consultation block may store, among other data, information corresponding to one or more consultations that are required to or desired to occur (or that have occurred) for the particular patient and the particular product. In some embodiments, a consultation block may correspond to a particular patient and to multiple products.

At a block 805, the method 800 may generate a consultation entry for each consultation that is required or desired to occur (or that has occurred) for the particular patient and the particular product. Information corresponding to the consultation entry (e.g., corresponding to fields 312a-312h) may be received and stored in the consultation entry, and the consultation entry may be stored in conjunction with a respective consultation block.

At a block 808, a request for consultation compliance information (e.g., a compliance request) may be received. The request may be received, for example, via a user input or a message from another computing device. The request may be for one or more specific consultation entries in their entirety, such as illustrated in FIGS. 15A and 15B, so that the one or more specific consultation entries may be audited. The request may be for a set of consultation entries that meet one or more particular compliance criteria (e.g., DUR review completed by a registered pharmacist, system generated consultations for all prescriptions for Drug Z, etc.), and/or for one or more consultation entries that do not meet the particular compliance criteria. The request may be for a set of consultation entries that include fields or portions that match a particular set of parameter values, such as illustrated in FIG. 15C. At a block 810, entries corresponding to the compliance request received at the block 808 are determined, and at a block 812, a response (e.g., a compliance response) indicating the entries determined at the block 810 may be sent to the requestor.

The method 800 allows for simple and quick determination of pharmaceutical consultation compliance. Currently used audit techniques for pharmaceutical consultation compliance typically spot-check single prescription orders for compliance. With the method 800, however, and in particular, by using the consultation blocks and entries generated at the blocks 802 and 805, compliance to pharmaceutical consultations (or non-compliance, as the case may be) can be quickly determined, reported, and audited from a wider perspective. For example, consultation activities may be tracked and/or audited by pharmacy location, by consultation type, by resolution type, or by authorizing party. In fact, consultation activities may be tracked and/or audited based on any number or combination of the fields 312a-312h of the consultation entries. Consultation activities may be tracked and/or audited based on values of any number or combination of the fields 312a-312h of the consultation entries. Of course, auditing or review of single consultation block or even a single consultation entry is feasible using the method 800. Accordingly, the method 800 allows for a pharmaceutical enterprise to audit and review pharmaceutical consultation data at varying levels and viewpoints to help the pharmaceutical enterprise in making better management decisions.

Although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A method for providing comprehensive pharmaceutical consultations, comprising:

generating, by a computing device, a consultation recording block corresponding to a single filling of a single prescription order corresponding to a drug prescribed for a patient, the single filling of the single prescription order including a work flow tracked by the computing device and having a plurality of stages including a data entry stage, a drug utilization review stage, a prescription order fill stage, a third party validation stage, and a payment stage, the consultation recording block including two or more consultation entries respectively corresponding to different stages of the work flow of the single filling of the single prescription order, each of the two or more consultation entries having a plurality of portions including a status portion indicating a status of a respective consultation, a first consultation entry of the two or more consultation entries corresponding to a first stage of the work flow of the single filling of the single prescription order, and a second consultation entry of the two or more consultation entries corresponding to a second stage of the work flow of the single filling of the single prescription order;

storing the consultation recording block in a memory accessible by the computing device;

displaying, on a display device coupled to the computing device, at least one of the two or more consultation entries;

receiving, via a user input interface coupled to the display device, information corresponding to at least one of the plurality of portions of the at least one of the two or more consultation entries, including:

receiving a first information corresponding to at least one of the plurality of portions of a first consultation entry of the at least one of the two or more consultation entries, and receiving a first authorization corresponding to the first information; and receiving a second information corresponding to at least one of the plurality of portions of a second consultation entry of the at least one of the two or more consultation entries, and receiving a second authorization corresponding to the second information; and storing the received information in the at least one of the two or more consultation entries of the consultation recording block.

2. The method of claim 1, wherein generating the first consultation entry corresponding to the first stage of the work flow comprises automatically generating, using the computing device, the first consultation entry based on an entry into or an exit from the first stage of the work flow.

3. The method of claim 1, wherein generating the first consultation entry corresponding to the first stage of the work flow comprises generating, using the computing device, the first consultation entry based on a user request received at the user input interface.

4. The method of claim 1, wherein one of the first authorization or the second authorization corresponds to a pharmacist's authorization, and the other of the first authorization or the second authorization corresponds to a non-pharmacist's authorization.

5. The method of claim 1, wherein at least one of:
receiving the information corresponding to the at least one of the plurality of portions includes receiving an indication of the status of the respective consultation,
the plurality of portions further includes a resolution portion, and receiving the information corresponding to the at least one of the plurality of portions includes receiving an indication of a resolution of the respective consultation, or
the plurality of portions further includes a comment portion, and receiving the information corresponding to the at least one of the plurality of portions includes receiving an indication of an acknowledgement of information displayed in the comment portion.

6. The method of claim 1, wherein information displayed in at least one of the plurality of portions of the at least one of the two or more consultation entries is based on data retrieved from a database corresponding to a particular stage of the plurality of stages of the work flow.

7. The method of claim 1, further comprising auto-filling at least a part of at least one of plurality of portions of the at least one of the two or more consultation entries.

8. The method of claim 1, wherein at least a part of the method is performed in conjunction with any stage of the work flow.

9. The method of claim 1, further comprising at least one of:
simultaneously displaying, on the display device, the two or more consultation entries;
displaying, on the display device, an indicator other than the two or more consultation entries that indicates an existence of the consultation recording block; or
displaying the consultation recording block in conjunction with another consultation recording block corresponding to the patient, the another consultation recording block corresponding to another prescription order for the patient or to a service.

10. A system for providing comprehensive pharmaceutical consultation, comprising:
a computing device including a memory and a processor; a display device communicatively coupled to the computing device; and
computer-executable instructions stored on the memory of the computing device and executable by the processor configured for:
generating a consultation recording block corresponding to a single filling of a single prescription order corresponding to a drug prescribed for a patient,
the single filling of the single prescription order corresponding to a work flow tracked by the computing device and having a plurality of stages including a data entry stage, a drug utilization review stage, a prescription
order fill stage, a third party validation stage, and a payment stage,
the consultation recording block including two or more consultation entries corresponding to the work flow of the single filling of the prescription order,
each of the two or more consultation entries corresponding to a different consultation associated with a respective stage of the work flow of the single filling of the single prescription order, and the each of the two or more consultation entries having a plurality of portions including a status portion indicating a status of a respective consultation and an authorization portion indicating an authorization of a completion of the respective consultation,
a first consultation entry of the two or more consultation entries corresponding to a first stage of the work flow of the single filling of the single prescription order; and
a second consultation entry of the two or more consultation entries corresponding to a second stage of the work flow of the single filling of the single prescription order;
storing the consultation recording block in the memory of the computing device or in another memory accessible by the computing device;
displaying, on the display device, at least one of the two or more consultation entries;
receiving information corresponding to at least one of the plurality of portions of the at least one of the two or more consultation entries, including:
receiving a first information corresponding to at least one of the plurality of portions of a first consultation entry of the at least one of the two or more consultation entries, and receiving a first authorization corresponding to the first information; and
receiving a second information corresponding to at least one of the plurality of portions of a second consultation entry of the at least one of the two or more consultation entries, and receiving a second authorization corresponding to the second information; and
populating the at least one of the two or more consultation entries of the consultation recording block with the received information.

11. The system of claim 10, wherein the information corresponding to at least one of the plurality of portions of the at least one of the two or more consultation entries is at least one of: received via a user input interface coupled to the display device, or received based on an access of a database by the computing device.

12. The system of claim 11, wherein the database accessed by the computing device is a particular database corresponding to at least one particular stage of the plurality of stages of the work flow.

13. The system of claim 10, wherein the first consultation entry is one of: automatically generated by the computing device based on an entry into or an exit from the first stage of the work flow, or generated by the computing device based on a user request received at a user input interface coupled to the display device.

14. The system of claim 10, further comprising further computer-executable instructions for at least one of:
simultaneously displaying, on the display device, the two or more consultation entries;
displaying, on the display device, an indicator other than the two or more consultation entries that indicates an existence of the consultation recording block; or
displaying, on the display device, the consultation recording block in conjunction with another consultation recording block corresponding to the patient, the another consultation recording block corresponding to another prescription order for the patient or to a service.

15. A system for providing comprehensive pharmaceutical consultation, comprising:
a computing device;

a consultation recording block corresponding to a single filling of a single prescription order for a drug prescribed for a patient and including two or more consultation entries, each of the two or more consultation entries corresponding to a respective different consultation corresponding to the single filling of the single prescription order, each of the two of more consultation entries having a plurality of portions including a status portion for indicating a status of a respective consultation, a resolution portion for indicating a resolution of the respective consultation, a comment portion for displaying stored information corresponding to the drug, and an authorization portion for receiving an authorization of the respective consultation, and a first consultation entry of the two or more consultation entries corresponding to a first stage of a plurality of stages of a work flow tracked by the computing device and corresponding to the single filling of the single prescription order, and a second consultation entry of the two or more consultation entries corresponding to a second stage of the plurality of stages of the work flow corresponding to the single filling of the single prescription order;

a display device coupled to the computing device and presenting at least a portion of the consultation recording block;

a user input interface coupled to the display device and configured to receive information corresponding to at least one of the plurality of portions of the at least one of the two or more consultation entries which includes:

a first information corresponding to at least one of the plurality of portions of a first consultation entry of the at least one of the two or more consultation entries, and receiving a first authorization corresponding to the first information; and a second information corresponding to at least one of the plurality of portions of a second consultation entry of the at least one of the two or more consultation entries, and receiving a second authorization corresponding to the second information; and a data storage entity accessible by the computing device and storing the consultation recording block and the information received using the user input interface.

16. The system of claim 15, wherein:

at least one of the first consultation entry or the second consultation entry is automatically presented on the display device when the single filling of the single prescription order enters into or exits from a respective stage of the work flow; and at least one of the plurality of portions of the automatically presented at least one of the first consultation entry or the second consultation entry is at least partially populated with an auto-filled character string.

17. The system of claim 16, wherein the auto-filled character string is based on data retrieved from a database corresponding to the respective stage of the work flow.

18. The system of claim 15, further comprising a cessation of a progression through the plurality of stages of the work flow corresponding to the single filling of the single prescription order when one of the two or more consultation entries is unpopulated, and a resumption of the progression through the plurality of stages when the one of the two or more consultation entries is at least partially populated.

* * * * *